(12) United States Patent
Bhavaraju et al.

(10) Patent No.: US 10,279,156 B2
(45) Date of Patent: May 7, 2019

(54) AUTO-REPLENISHING, WOUND-DRESSING APPARATUS AND METHOD

(71) Applicant: Aplion Medical Corporation, Salt Lake City, UT (US)

(72) Inventors: Sai Bhavaraju, West Jordan, UT (US); John Howard Gordon, Salt Lake City, UT (US); Jeremy Heiser, Salt Lake City, UT (US); Ashok V Joshi, Salt Lake City, UT (US); Troy C Dayton, Syracuse, UT (US)

(73) Assignee: Aplion Medical, LLC, Salt Lake City, UT (US)

( * ) Notice: Subject to any disclaimer, the term of this patent is extended or adjusted under 35 U.S.C. 154(b) by 1176 days.

(21) Appl. No.: 14/305,995

(22) Filed: Jun. 16, 2014

(65) Prior Publication Data

US 2014/0296774 A1  Oct. 2, 2014

Related U.S. Application Data

(62) Division of application No. 12/341,832, filed on Dec. 22, 2008.

(Continued)

(51) Int. Cl.
*A61M 35/00* (2006.01)
*A61F 13/40* (2006.01)
*A61F 13/00* (2006.01)

(52) U.S. Cl.
CPC ....... *A61M 35/00* (2013.01); *A61F 13/00068* (2013.01); *A61M 35/006* (2013.01);
(Continued)

(58) Field of Classification Search
CPC ...... A61F 2013/0017; A61F 13/00068; A61M 35/00
(Continued)

(56) References Cited

U.S. PATENT DOCUMENTS 4,090,514 A   5/1978  Hinck
4,136,696 A   1/1979  Nehring
(Continued)

FOREIGN PATENT DOCUMENTS

DE   4012232 A1   10/1991
EP   0020662      7/1984
(Continued)

OTHER PUBLICATIONS

Kim, Tae San "Written Opinion of the International Searching Authority", International App. No. PCT/US2008/088044, 1-5.
(Continued)

*Primary Examiner* — Susan Su
(74) *Attorney, Agent, or Firm* — Patterson Intellectual Property Law, PC; Hilary Dorr Lang; Edward D. Lanquist, Jr.

(57) ABSTRACT

Apparatus and methods to treat skin defects include a pump with reservoirs for a pressurization gas and a fluid. Upon activation, the pump generates a gas introduced into the gas reservoir, a movable wall of which displaces a movable wall of a fluid source, thus dispensing the fluid into the dressing to spread throughout irrespective of orientation of the dressing, maintaining a transport fluid (e.g. carrier) in the dressing and in contact with a skin defect being treated. The dressing may have a distribution network, and multiple members, dispensing the fluid into the dressing and in contact with a skin defect being treated.

20 Claims, 9 Drawing Sheets

Related U.S. Application Data

(60) Provisional application No. 61/015,952, filed on Feb. 27, 2008.

(52) U.S. Cl.
CPC . *A61F 2013/002* (2013.01); *A61F 2013/0017* (2013.01); *A61F 2013/00174* (2013.01); *A61F 2013/00268* (2013.01)

(58) Field of Classification Search
USPC ......... 604/149, 150, 245, 304–308, 317–326
See application file for complete search history.

(56) References Cited

U.S. PATENT DOCUMENTS

| | | | |
|---|---|---|---|
| 4,194,041 A | 3/1980 | Allen, Jr. et al. | |
| 4,382,441 A | 5/1983 | Svedman | |
| 4,657,160 A | 4/1987 | Woods et al. | |
| 4,735,613 A | 4/1988 | Bellin et al. | |
| 4,969,874 A | 11/1990 | Michel et al. | |
| 4,969,880 A | 11/1990 | Zamierowski | |
| 5,090,963 A | 2/1992 | Gross et al. | |
| 5,147,310 A | 9/1992 | Giannini et al. | |
| 5,152,757 A | 10/1992 | Eriksson | |
| 5,176,663 A | 1/1993 | Svedman et al. | |
| 5,186,805 A | 2/1993 | Gross et al. | |
| 5,318,540 A | 6/1994 | Athayde et al. | |
| 5,318,557 A | 6/1994 | Gross | |
| 5,346,477 A | 9/1994 | Edwards et al. | |
| 5,358,494 A | 10/1994 | Svedman | |
| 5,460,243 A | 10/1995 | Patterson | |
| 5,492,534 A * | 2/1996 | Athayde ............... | A61M 5/148 604/141 |
| 5,567,287 A | 10/1996 | Joshi et al. | |
| 5,573,646 A | 11/1996 | Saito et al. | |
| 5,611,779 A | 3/1997 | Saito et al. | |
| 5,700,254 A | 12/1997 | McDowall et al. | |
| 5,707,499 A | 1/1998 | Joshi et al. | |
| 5,741,275 A | 4/1998 | Wyssmann | |
| 5,759,570 A | 6/1998 | Arnold | |
| 5,785,688 A | 7/1998 | Joshi et al. | |
| 5,891,097 A | 4/1999 | Saito et al. | |
| 5,899,381 A | 5/1999 | Gordon et al. | |
| 5,983,136 A | 11/1999 | Kamen | |
| 6,042,704 A | 3/2000 | Joshi et al. | |
| 6,045,055 A | 4/2000 | Joshi et al. | |
| 6,060,196 A | 5/2000 | Gordon et al. | |
| 6,071,267 A | 6/2000 | Zamierowski | |
| 6,169,223 B1 | 1/2001 | Mahr et al. | |
| 6,220,267 B1 | 4/2001 | Joshi | |
| 6,398,767 B1 | 6/2002 | Fleischmann | |
| 6,413,238 B1 | 7/2002 | Maget | |
| 6,415,808 B2 | 7/2002 | Joshi | |
| 6,458,109 B1 | 10/2002 | Henley et al. | |
| 6,520,936 B1 | 2/2003 | Mann | |
| 6,530,900 B1 | 3/2003 | Daily et al. | |
| 6,575,961 B2 * | 6/2003 | Joshi ............... | A61M 5/14244 424/438 |
| 6,695,824 B2 | 2/2004 | Howard et al. | |
| 6,767,334 B1 | 7/2004 | Randolph | |
| 6,787,008 B2 | 9/2004 | Joshi et al. | |
| 6,824,528 B1 | 11/2004 | Faries, Jr. et al. | |
| 6,890,553 B1 | 5/2005 | Sun et al. | |
| 7,077,832 B2 | 7/2006 | Fleischmann | |
| 7,112,712 B1 | 9/2006 | Ancell | |
| 2001/0031943 A1 | 10/2001 | Urie | |
| 2002/0068913 A1 | 6/2002 | Fleischmann | |
| 2002/0150720 A1 | 10/2002 | Howard et al. | |
| 2002/0161346 A1 | 10/2002 | Lockwood et al. | |
| 2002/0183702 A1 | 12/2002 | Henley et al. | |
| 2003/0040687 A1 | 2/2003 | Boynton et al. | |
| 2003/0149406 A1 | 8/2003 | Martineau et al. | |
| 2003/0225441 A1 | 12/2003 | Boynton et al. | |
| 2004/0076662 A1 | 4/2004 | Riesinger | |
| 2004/0087916 A1 | 5/2004 | Pickup et al. | |
| 2004/0126413 A1 | 7/2004 | Sigurjonsson et al. | |
| 2005/0023371 A1 | 2/2005 | Joshi et al. | |
| 2005/0058711 A1 | 3/2005 | Massengale et al. | |
| 2005/0125035 A1 | 6/2005 | Cichocki, Jr. et al. | |
| 2005/0147654 A1 | 7/2005 | Matloub et al. | |
| 2006/0116620 A1 | 6/2006 | Oyaski | |
| 2006/0155260 A1 | 7/2006 | Blott et al. | |
| 2006/0255063 A1 | 11/2006 | Gallnbock | |
| 2007/0021698 A1 | 1/2007 | Fleisch Mann | |
| 2007/0032762 A1 | 2/2007 | Vogel | |
| 2007/0066945 A1 | 3/2007 | Martin | |
| 2007/0239078 A1 | 10/2007 | Jaeb | |

FOREIGN PATENT DOCUMENTS

| | | |
|---|---|---|
| EP | D020662 B1 | 7/1984 |
| GB | 2416909 | 2/2006 |
| GB | 2416909 A | 2/2006 |
| WO | 9100718 A1 | 1/1991 |
| WO | WO9100718 | 1/1991 |
| WO | 2005102415 A1 | 11/2005 |
| WO | 2005105180 A1 | 11/2005 |
| WO | WO2005102415 | 11/2005 |
| WO | WO2005105180 | 11/2005 |
| WO | 2006114638 A2 | 11/2006 |
| WO | WO2006114638 | 11/2006 |
| WO | WO2006114648 | 11/2006 |
| WO | 2007031762 A1 | 3/2007 |
| WO | WO2007031762 | 3/2007 |

OTHER PUBLICATIONS

Kim, Tae San "International Search Report", International App. No. PCT/US2008/088044, 1-5.
Segerberg, Tomas "EP Search Report", App. No. 08872795, (dated May 25, 2011), 1-9.
Segerberg, Tomas "Communication Pursuant to Article 94(3) EPC", EP 08872795.3 Office Action (corresponding to U.S. Appl. No. 12/341,832, (dated Jan. 30, 2012), 1-4.
Teder et al, "Continuous Wound Irrigation in the Pig", Journal of Investigative Surgery, 1990, pp. 399-407, vol. 3, United Kingdom.
Svedman, "A Dressing Allowing Continuous Treatment of a Biosurface", IRCS Medical Science: Biomedical Technology; Clinical Medicine; surgery and Transplantation, 7, 221, 1979.
Svedman, "Irrigation Treatment of Leg Ulcers", The Lancet, Sep. 3, 1983, pp. 532-534.
Arnljots et al., "Irrigation Treatment in Split-Thickness Skin Grafting of Intractable Leg Ulcers", Scand J Plast Reconstr Surg 19:211-213, 1985.
Svedman, P. "Irrigation Treatment of Leg Ulcers," P. Svedman; The Lancet, Sep. 3, 1983 p. 532-534.
Teder, H. et al."Continuous Wound Irrigation in the Pig," Journal of Investigative Surgery, 1990, vol. 3, pp. 399-407.
Svedman, P. "A Dressing Allowing Continuous Treatment of a Biosurface," ICRS Med. Sci. Biomed Technol., 1979, 7:221.
Arntiots, B. "Irrigation Treatment in Split-Thickness Skin Grafting of Intractable Leg Ulcers," Scand. J. Plast. Reconstr. Surg. 1985, 19:211-213.
Opposition Proceedings for EP2244746—Notice of Opposition Form Hartmann dated Jul. 31, 2013.
Opposition Proceedings for EP2244746—Notice of Opposition Form Rasmussen dated Jul. 31, 2013.
Opposition Proceedings for EP2244746 —Notice of Opposition Grounds Hartmann dated Apr. 28, 2014.
Opposition Proceedings for EP2244746 Notice of Opposition Grounds Rasmussen dated Apr. 30, 2014.
Opposition Proceedings for EP2244746—Reply to Opposition dated Dec. 2, 2014.
Opposition Proceedings for EP2244746—Reply from Patentee to Opposition dated Dec. 3, 2014.
Opposition Proceedings for EP2244746—European Patent Office Communication dated Oct. 6, 2015.

(56) References Cited

OTHER PUBLICATIONS

Opposition Proceedings for EP2244746—Letter regarding Opposition Procedure from Patentee dated Oct. 5, 2016.
Opposition Proceedings for EP2244746—Written Submission of Patentee dated Oct. 19, 2016.
Opposition Proceedings for EP2244746—Letters from Hartmann and Rasmussen and attached annexes dated Oct. 21, 2016.
Opposition Proceedings for EP2244746—Minutes of Oral Proceedings dated Dec. 20, 2016.
Opposition Proceedings for EP2244746—Amended description dated Feb. 27, 2017.
Opposition Proceedings for EP2244746—EPO Communication dated Sep. 12, 2017.
Opposition Proceedings for EP2244746—Decision dated May 02, 2018.
Opposition Proceedings for EP2244746 - Final Decision dated Oct. 12, 2018.

* cited by examiner

AUTO-REPLENISHING, WOUND-DRESSING APPARATUS AND METHOD

RELATED APPLICATIONS

This application is a divisional of, and claims priority to, U.S. patent application Ser. No. 12/341,832, filed on Dec. 22, 2008, which application is related to and claims the benefit of U.S. Provisional Patent Application Ser. No. 61/015,952 filed on Feb. 27, 2008. These applications are incorporated herein by reference.

U.S. GOVERNMENT INTEREST

This invention was made with government support under Contract No. W81XWH-05-1-0484 awarded by the U.S. Army Medical Research and Material Command Department of Defense. The government has certain rights in the invention.

BACKGROUND

The Field of the Invention

This invention relates to treatment of skin defects, and in particular to control and delivery of treatment substances to a dressing on a skin defect.

The Background Art

Skin defects may be inflicted by people, machines, tools, vehicles, animals, plants, the environment, and many other factors. Likewise, pressure, ailments, infections, and disease may create sores, open wounds, and other skin defects. Skin defects may be treated by a variety of physical processes, materials, conditions, controls, and the like, each based on a particular theory, experiment, regimen, or other basis of justification. Meanwhile, skin defects may be characterized by their significance or seriousness, as well as their nature, their susceptibility to treatment, or the like. Skin defects maybe defined as wounds, incisions, or an injury to the body (as from trauma, pathology, or surgery) that typically involves laceration or breaking of a membrane (as the skin or mucous membrane) and usually damage to underlying tissues. Furthermore a wounds or skin defect may be characterized as minor, superficial, major, traumatic, acute, chronic, fatal, or the like.

Skin defects may require isolation from an environment, exposure to a particular environment, treatment by exposure to a medicament, covering, uncovering, and so forth. One area of continuing interest is the treatment of skin defects by applying a dressing. Typically, treatment may include some type of anti-sepsis process. After application of medicament such as an antiseptic, antibiotic, or the like in tincture or ointment form, a bandage or other covering may be applied to control or limit access to the skin defects by environmental agents (e.g. air, dirt, touching, etc.).

In treating skin defects, applying a medicament may only solve part of the problem. Changing a dressing, replenishing a quantity or concentration of a medicament, controlling the access, contact, and concentration of an active ingredient applied to skin defects, and verification of the foregoing are typically difficult to do. Application of a constant or even reliable or consistent concentration of a medicament is difficult to accomplish, even for a regularly attended patient.

For example, application of a salve, ointment, cream, irrigation, tincture, or the like occurs at a point in time. The dressing itself may soak up the medicament fluid, removing the contact with the skin defects. Drying of a carrier portion of a medicament fluid may inhibit chemical activity of an active ingredient by removing the necessary transport fluid required for migration, diffusion, or the like. Drying of tissues, blood, or serum may inhibit the action or effectiveness of an active ingredient, and may even block access by an active ingredient to underlying skin defect. Thus, finding a proper delivery mechanism to consistently, regularly, or constantly apply the right amount of a therapeutically effective active ingredient may be problematic in many instances.

Once a medicament fluid is applied as a salve, liquid, tincture, aspersion, cream, irrigation, or the like, the problem of the concentration of the active ingredient may actually render the application ineffective relatively quickly. Many medicaments, once applied, have a rapidly decaying, uncontrolled, or ineffective concentration. Subsequently the concentration of an active ingredient in the bulk of a medicament fluid is necessarily much higher than the concentration migrating to the affected skin defect area. Thus the delivered concentration may become inappropriate. Some dressings e.g. impregnated dressings deliver either below the therapeutic range or above it causing inadequate treatment or side effects and in the case of antibiotics possible resistance.

Accordingly, what is needed is a method and system for consistent delivery over time of a specific volume, specific concentration and/or therapeutically effective concentration of an active ingredient of a beneficial fluid to the site of skin defect. Also desirable would be supplying a specific volume, specific concentration and/or therapeutically effective concentration of a fresh active ingredient in a programmable manner to be within the therapeutic window to eliminate effects due to under delivery or over delivery. Also desirable is a method for maintaining a transport fluid (e.g. carrier, moisture, tissue moisture, etc.) available to support delivery of the active ingredient to the skin defect. It would be an advance in the art to provide a system and method to maintain a prescribed transport path, and effective concentration of fresh active ingredient to the site of the skin defect.

BRIEF SUMMARY OF THE INVENTION

In accordance with the foregoing, an apparatus and method in accordance with the invention may include a fluid delivery system that includes a housing with reservoirs for a pressurization gas and sources for a medicament fluid. The fluid may be loaded into a reservoir at a factory and sealed, or may be filled at the point of use through a valve, septum, or the like. Filling the device at the point of use includes the ability to select from fluids containing a variety of appropriate fresh actives or combinations thereof. Point of use or in situ filling has the added advantage of separating the shelf life and handling requirements of the device from the self life and handling requirements of the active. This may also be referred to as In situ filling.

The system of fluid delivery may include a housing having an inextensible interior volume to contain reservoirs and fluid sources in contact with one another. A fluid source may have a wall flexible or otherwise able to move in response to pressure, being sealed to contain and maintain a fluid comprising an active ingredient disposed in a fluid carrier. An inlet port, such as a septum may provide sterile access to the fluid source to introduce the fluid. An outlet port is provided for the fluid source to dispense the fluid.

A reservoir containing a gas moves at least one wall in response to pressure from gas output of a galvanic cell within or outside, but in communication with the reservoir. An electric circuit may control current flow to control the rate of generation of gas. The circuit may use a resistor and switch, a more sophisticated control circuit, or a microprocessor controller to control current and thus the gas generation rate. The electrical circuit may be within the reservoir or within the housing or outside the housing. The electrical circuit may be controlled remotely or directly, by electrical, electromagnetic, magnetic, optical or mechanical means.

An outlet dispenses the fluid from the fluid source in response to displacement of its wall by the gas reservoir, sending the fluid through a feed conduit to a dressing. The term conduit, feed conduit, feed line, and tubing may be used interchangeably throughout this disclosure. The feed conduit may be as short or as long as desired, supporting placement of the pump nearby, or remote from, the dressing. The feed conduit may include a restricted tube providing resistance to the fluid flow, thereby establishing back pressure within the fluid source. By selection of appropriate tubing and flow rate, a certain value of back pressure can be established within the fluid source.

Upon activation, the fluid delivery system may generate a gas into the gas reservoir having a movable wall. The movable wall of the gas reservoir exerts pressure and displacement against a movable wall of the fluid source or reservoir, thus displacing the fluid. It will be appreciated by those of skill in the art that the combination of the housing, gas reservoir, and fluid source may be configured as a pump or pump mechanism. The displaced fluid may pass through a feed conduit to a dressing and ultimately to a skin defect to which the dressing is applied.

The dressing may include a distribution member which may be a wicking layer, a manifold of tubes with apertures, or a pouch with pores that allows the fluid to be distributed substantially uniformly irrespective of orientation of the dressing. In one embodiment, the distribution member maintains a fluid in the dressing and in contact with the skin defect being treated. The fluid may be a transport fluid or carrier for conveying an active ingredient to the skin defect.

A connector positioned on the dressing connects the feed conduit to a distribution member portion of the dressing. The connector may be advantageously positioned centrally on the dressing even though it may be anywhere on the dressing. The distribution member may distribute the fluid there across, maintaining substantially even wetting across the domain irrespective of orientation of the dressing. The fluid may saturate the wicking portion, thus making the fluid available to be in intimate contact with the skin defect. The orientation independence of the wicking member may be accomplished by implementing various effects, including capillary action, hydrophobic/hydrophilic nature of the layer, surface tension optimization, composition, or texture and weave patterning of the layer, or the effects of evaporation. These effects individually or in combination are referred to "wicking action."

When the distribution member is a manifold, the fluid may exit the feed conduit and into a manifold and exit substantially evenly through the apertures irrespective of orientation by maintaining a high fluid pressure in the manifold relative to barometric pressure. The fluid may also be delivered substantially evenly through the pores in the pouch due to the comparatively high and uniform pressure across the plenum created by the pouch. A specific volume, specific concentration and/or therapeutically effective concentration, or in other words a predetermined range of concentration, of the active ingredient may thus be available and in intimate contact with the skin defect, providing a transport fluid, active ingredient, constant rate, controllable and renewable concentration, and intimate contact. The terms manifold, header, arms, distribution tubes, tree structure, and plenum are used interchangeably throughout this specification.

The dressing may function effectively with any generic source other than the specific pump system described herein. Therefore, the source may be manual, such as a syringe, or any other delivery mechanism including gravity feed, mechanical pumping etc. The source can supply fluid continuously, discontinuously, programmably, manually, or the like.

In one embodiment, the dressing is configured to be cut to size, and still maintain the functional properties of the dressing. This will allow the dressing to be adaptable to the size of the skin defect.

The fluid may be configured as a liquid having an active ingredient dissolved within the liquid, or suspending as a micro-pulverized particulate, all disposed within a liquid having a viscosity selected to optimize a therapeutic effect a fluid may have a viscosity ranging from a very thick, honey-like substance, to a comparatively aqueous like, such as water or other liquid base. Furthermore, a fresh active is a quality of material that remains substantially in its original state and has not been degraded. A fresh active may also be provided in quantities that need not anticipate such degradation or change in the kinetics of delivery. For the purposes of this disclosure the terms fluid, fresh active, and medicament may be used in similar manners discernable by one schooled in the art. A medicament maybe a fluid or it may be in some other form.

The active ingredient may be an agent having antimicrobial, antibiotic, analgesic, anti-inflammatory, hydrating, growth promotion, enzymatic debridement, antiseptic, irrigation, anesthetic, or emollient effect, and may be systemic, penetrating, or topical. The fluid carrier of the fluid may be a liquid, gas, gel, sol, thixotropic, colloid, or other fluid, and may carry the active ingredient dissolved therein or suspended as particles in suspension.

The housing may be substantially rigid and made of metal, metal alloy, polymer, reinforced polymer, ceramic, or the like. Steel, stainless, brass, bronze, aluminum, titanium, and copper as well as olefinic, styrenic, polycarbonate, and elastomeric hydrocarbons may serve adequately. The housing may be transparent to visible light, which may provide sight monitoring, but opacity may provide protection of the integrity of the fluid. The housing may not be gas tight, but vented, thus allowing point of use filling of the fluid source or other actions expelling gas from the housing during operation.

Any reservoir or fluid source may have a pressure-relief mechanism, such as a vent or check valve, to regulate pressure, resist backflow, prevent rupture, or the like. The fluid source may be filled by a syringe, through a valve or septum, and may be overfilled in order to prime the feed conduit, the dressing, or both prior to activation of the gas generator. Reservoirs or fluid sources may be permanent or replaceable, single use or refillable, or the like. Likewise, the housing may be disposable or reusable, sealed, or openable. The gas present in the reservoir may be vented at any time. The fluid source may be pre-filled or filled at the point of use, and disposable or refillable. The point of use capability allows the user to select the suitable treatment among many options and greatly extends shelf life.

Gases from the gas generator may be any of those readily generated by electrochemical means. For example hydrogen, oxygen, nitrogen, or carbon dioxide may be generated by galvanic cells without any need for external power. Typically, for a gas phase device with higher operating pressure comes less sensitivity to the environment, particularly the effects of changes in ambient temperature and pressure are proportionately lessened with higher operating pressures. Greater than ambient operating pressure substantially improves the precision and accuracy of the device performance. Significantly higher operating pressures reduce the ambient effects substantially.

The gas generator may include a galvanic cell completely contained within the gas reservoir. The gas reservoir may be formed of a dielectric material to further insulate the electric circuit inside. The circuit may be outside the reservoir or even outside the housing, but sealing may be easier if no penetrations are required in the wall or seams or the reservoir. Actuation may be direct or remote, from a mechanical force, magnetic field, electric pulse, radio frequency signal, acoustic wave, or the like. Any activity of the apparatus may be indicated by an indicator identifying an "on" condition.

The feed conduit may be formed to be substantially inextensible, or may respond to pressure by including a pressure accumulator or simply an elastic portion to expand to ameliorate any sudden increase in pressure In use, an apparatus having a housing and a flexible reservoir and fluid source may have a selected fluid introduced as a fluid, and may be filled in a manner to prime the feed conduit, dressing, or both by injecting the fluid into the fluid source. Filling may pressurize the fluid source and force open a check valve, filling the feed conduit, and partially filling or saturating the dressing. Filling may also result in the initial pressurizing of the fluid source, expediting the need for the gas bag to do so and decreasing start up time.

The distribution member may be a manifold that distributes the fluid to various regions of the wick portion thereof. Tubes having perforations or orifices to resist flow may maintain a substantially equal pressure inside the distribution manifold. Sizes of path lengths, diameters, orifices, or the like may control pressure among outlets of tubes, plenums, pouches, bags, or the like to effect even distribution of the fluid.

A multi-member dressing may include a distribution member that may be a wicking layer receiving the fluid, a protective member that may or may not be configured to protect the dressing from the environment and provide for vapor transmission, a transfer or transport member to transfer the fluid to the wicking layer, a fluid absorber to absorb excessive fluid being delivered or for absorbing the wound exudate, a tenting member positioned at the rim of the dressing to provide for lateral evaporation, and an interface member between the wicking layer and the treated skin defect to transfer the fluid thereto from the wicking layer while performing any other function needed, such as-anti-adhesion, or the like. Alternatively, the dressing may comprise at least one functional member consisting of a distribution member, and additionally an interface member, transport member, barrier member, fluid absorber, any of said members could be integrated to achieve multiple functions in one or more members.

An interface member may be formed as a sheet, foam, gel, gauze, porous matrix, honeycomb, mop of fibrous material, comminuted fibrous material, nanotube composite structure, or the like, or any combination thereof. The material thereof may be a biodegradable copolymer, dermal regeneration template, bioabsorbable gel, anti-adhesion polymer, skin substitute, moisture-retaining natural or synthetic composition, angiogenic composition, antimicrobial composition, or the like, or any combination thereof. The carrier along with the active ingredient may be delivered directly to the skin defect. Alternatively the active alone may be transferred to the skin defect by diffusion or migration. The current device allows maintenance of fluid balance in the skin defect under treatment. For example, moisture may be provided to the skin defect and excess moisture may be removed by vapor transmission or by an absorptive member. The interface layer may also be referred to as the non adhering layer.

The distribution member material may be a polymer sheet, woven fabric, non-woven fabric, naturally occurring fiber, sponge, fiber matrix, gauze, absorbent material, adsorbent material, gel, foam, or the like, or any combination thereof. Systems and methods in accordance with the foregoing may treat dermatological disorders, incisions or deeper wounds. For example embodiments of systems and methods in accordance with the invention may be useful for delivering a fluid prescribed for a cut, laceration, scrape, allergy eruption, skin cancer, rash, burn, undesirable growth, cyst, wart, tumor, ulcer, boil, irritation, incision, trauma or the like.

In general, a therapeutically effective concentration of an active ingredient may be delivered to the site of a disorder and delivered by intimate contact through the dressing. A pore size in a wicking portion of a dressing may be selected evenly distribute the fluid carrier containing the active ingredient, independent from orientation.

The described apparatus for delivering fresh fluids to the skin defects may also be coupled with other well known wound treatments such as debridement, negative pressure wound therapy, phototherapy, surgical treatments, compression therapy, tissue replacement or the like.

All the components in the described dressing have configurations that function independently from their orientation. Thus, the dressing or system as a whole may operate independent of orientation constraints.

The system is storage stable. Due to the stability of the mechanical and chemical systems, and the empty or closed nature of the mechanical systems, all may be stored for an extended period of time (e.g. months or years) before being put to use by point of use filling of the fluid source.

Whether delivered at a substantially constant rate, periodic dosage volume, feedback controlled saturation or moisture content, chemically detectable concentration, or by manual intervention, delivery of a pre-selected, therapeutically effective, threshold concentration may be prescribed. The rate may be at a threshold value or in a range. The control points for either a threshold value or a range may be selected, and the fluid delivered to effectively control pain, biotic growth, hydration, aeration, chemical reactions, biological process, or the like, or any suitable combination thereof.

Thus a periodically, constantly, or programmatically delivered amount of a fluid into a dressing may maintain intimate contact, a transport fluid, and a controllable concentration of fresh active ingredient to a site of skin defect. The term skin defect could be any dermatological disorder such as a wound, allergy eruption, skin cancer, rash, burn, undesirable growth, cyst, wart, tumor, ulcer, boil, irritation, incision, graft, oiliness, dryness, wrinkles, blemishes, discolorations, and trauma. The term "skin defect" may be used interchangeably with any of these terms throughout the specification, depending upon the context in which the term is used.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED PREFERRED EMBODIMENTS DESCRIPTION

Figure 1:
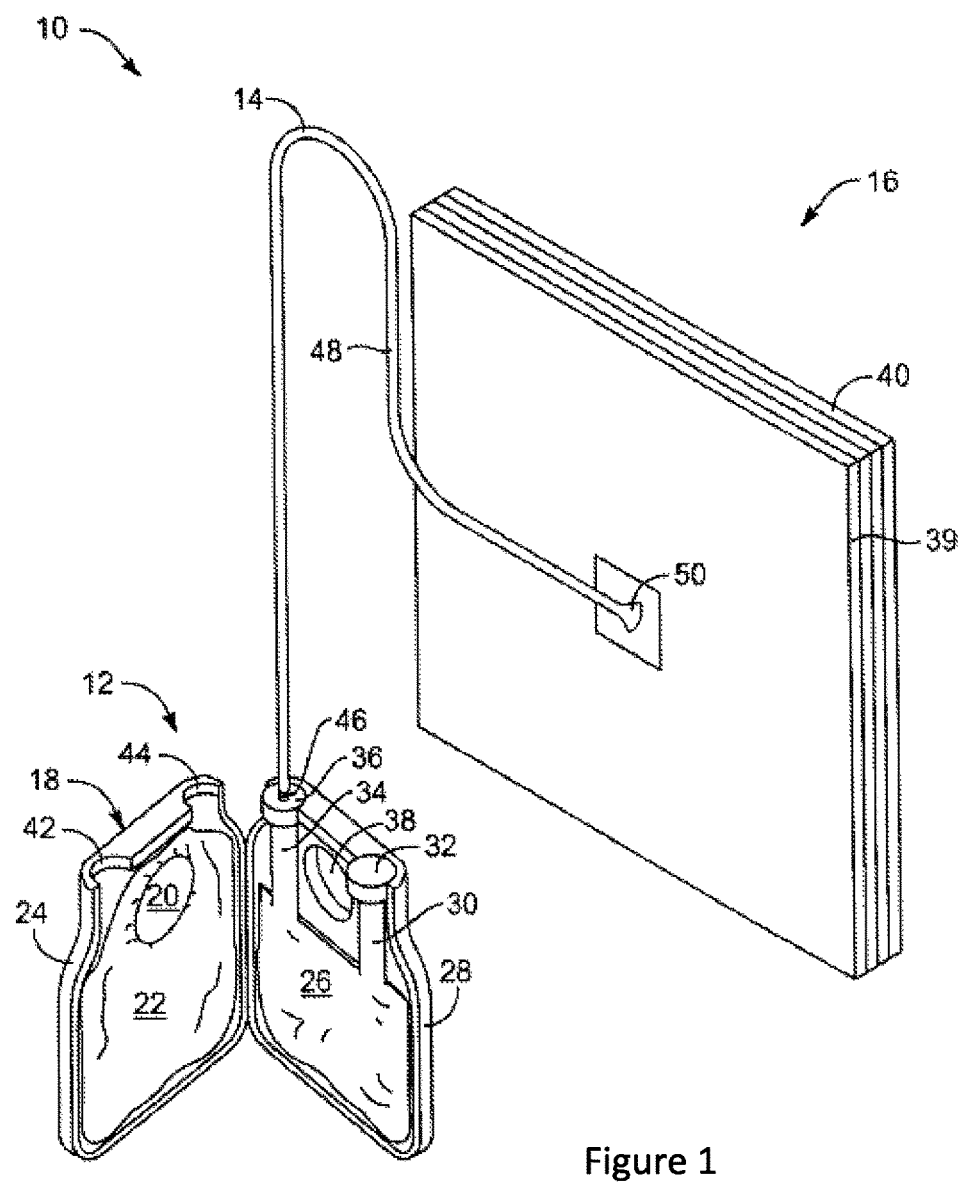
FIG. 1 is a perspective view of one embodiment of a fluid delivery system for delivery of a fluid to a dressing for a skin defect.

It will be readily understood that the components of the present invention, as generally described and illustrated in the drawings herein, could be arranged and designed in a wide variety of different configurations. Thus, the following more detailed description of the particular embodiments of the apparatus, systems, and methods in accordance with the present invention, as represented in the drawings, is not intended to limit the scope of the invention, as claimed, but is merely representative of various embodiments of the invention. The illustrated embodiments will be best understood by reference to the drawings, wherein like parts are designated by like numerals throughout, and trailing letters following a numeral simply indicate specific instances of the item identified by the corresponding reference numeral.

Referring to FIG. 1, an apparatus 10 or system 10 in accordance with the invention may include a pump 12 operating as a delivery mechanism 10 for a fluid. The fluid may typically be of a viscosity in a configuration suitable for pumping. Likewise, a fluid may be configured as a liquid having an active ingredient dissolved within the liquid, or suspending as a micro-pulverized particulate, all disposed within a liquid having a viscosity selected to optimize performance of the apparatus 10. For example, in one embodiment, the fluid or liquid operating within the pump 12 as a fluid may have a viscosity ranging from a very thick, honey-like substance, to a comparatively aqueous like viscosity, such as water or other liquid base.

In another embodiment, the fluid may be a gel containing gelatin or other gelling agents in a liquid solution to stabilize that solution against separation, evaporation, or the like. Accordingly, a medicament or active ingredient may be dissolved in a liquid, and the liquid may be stabilized with a gelling agent.

The active ingredient may include at least one composition chosen from an antimicrobial, an antibiotic, an antifungal, an antiviral, an antiseptic, and an antibacterial agent. The active ingredient may also include at least one composition chosen from an analgesic, a palliative, and an anti-inflammatory agent. In one embodiment, the active ingredient comprises at least one composition chosen from de-ionized water, a polymeric gel, a saline composition, and a hydrocolloid. The active ingredient may comprise at least one beneficial agent chosen from an enzymatic debrider, a tissue growth factor, a scar-reducing agent, tissue cells, topical nutrients, a coagulant, nitric oxide, oxygen gas, ozone, and a gene therapy agent. It will be appreciated by those of skill in the art that the active ingredient may be selected to be therapeutically effective in treating a dermatological disorder chosen from a skin defect, an allergy eruption, a skin cancer, a rash, a burn, a growth, a cyst, a wart, a tumor, an ulcer, a boil, an incision, a graft, oiliness, dryness, wrinkles, blemishes, discolorations, trauma, and numerous other maladies or conditions.

In general, an apparatus or fluid delivery system 10 may operate to deliver a fluid through a feed conduit 14 extending a distance appropriate to service a dressing 16. In certain embodiments, the fluid delivery system 10 may include a housing 18. The housing 18 may be made of any suitable material and manufacturing method. For example, various polymers may be formed by methods such as vacuum forming, injection molding, blow molding, casting, or the like in various suitable shapes to have an interior cavity of suitable shape.

The housing 18 may be made in one or more parts. For example, the housing 18 may be opened like a clam shell. Alternatively, the housing 18 may be formed as a single piece. In other embodiments, the housing 18 may be formed as a single piece having hinge portions and latch portions in order to close the housing 18 portions upon themselves in order to enclose the contents thereof.

The housing 18 may be formed as pieces, fabricated and assembled to be permanently closed. The housing 18 may also be manufactured by stamping, die casting, centrifugal casting, investment casting, or other methods used in forming polymers or metals.

The housing 18 may be formed to have an opaque appearance on one or both sides or halves, or may have a translucent or even transparent appearance. In a transparent configuration, the housing 18 may provide visibility of a fluid therein. Thus, a quick, visual inspection may provide feedback on whether the amount or condition of the fluid is suitable. Likewise, any malfunction or abnormality of operation of the pump 12 may be readily visible within the housing 18.

Polymer resins for injection molding may provide a comparatively lightweight and rigid structure for the housing 18. Likewise, however, various stamped or die cast metal parts may also provide a robust, rigid, strong housing 18 for containing pressurized fluids in containers. For convenience, having a comparatively small aspect ratio of thickness to length or of thickness to height, in housing 18, may benefit from a comparatively thicker wall.

Nevertheless, if a sufficiently light and strong material and construction configuration are used for the housing 18, an aspect ratio near unity may be appropriate as containment. For example, a hard, rigid housing 18 may provide protection against rupture or failure under the influence of accidental over-pressurization. This may be important in preventing an accidental bolus from being delivered due to crushing or compression of a compressible container within a compressible housing 18.

Nevertheless, such a safety or control issue may not be a problem when a housing 18 is connected by a clip or magnet to a bed frame, medical IV stand, or the like. Then, a simple containment vessel of a sack type or wire frame type may suitably act as a housing 18. On the other hand, a housing 18 may be exposed to pressure by being placed on the bed or under the pillow of a patient or in a pocket of the clothing worn by a patient. Then, the dynamics may dictate the necessity of a rigid housing 18 capable of withstanding external pressures.

In the illustrated embodiment, a gas generator 20 may provide an integrated source of gas to fill a reservoir 22. For example, the gas generator 20 may include an electrochemical cell. In one embodiment, the fluid delivery system 10 includes a galvanic cell in communication with the reservoir and comprising a chemical selected to produce a gas within the reservoir 22. Thus, a galvanic cell, in which a galvanic reaction occurs generating gas as a byproduct of the chemical reaction, is a suitable mechanism for a gas generator 20. In such embodiments, a control circuit may be an integrated portion of the gas generator.

In certain embodiments the gas generator 20 may be enclosed completely with the reservoir 22, thus easing the need for complex or unreliable sealing procedures and materials. That is, sealing different materials or hard materials to flexible materials, or the like may sometimes be problematic. Likewise, over time, seals may deteriorate, separate, or otherwise fail.

By contrast, if the gas generator 20 is integrated within an electrochemical cell, but then completely encapsulated within the reservoir 22, a switch or controller may be imbedded. Access may be obtained by applying pressure to the switch or controller through the wall of the reservoir 22, by pushing on it through an opening in the wall of the housing 18. In such a manner, control of the gas generator 20 may be exercised within a sealed system of the reservoir 22. Alternatively, a switch mounted to a circuit board is sealed contiguously onto the face of the reservoir 22 in such a manner to maintain the gas tight property of the reservoir 22. In certain embodiments the galvanic cell is enclosed in the reservoir 22 and the wires from the cell where connected to the circuit board positioned on the housing 18 wall allowing easy access to the circuit board.

An electrical conductor having various elements of control may run the galvanic cell to complete the circuit between the two reactant materials. A controller may be connected to the galvanic cell in a circuit to control the generation of the gas in the reservoir 22, thereby controlling a delivery rate of the fluid from the fluid source. The controller may comprise a fixed or variable resistor and a switch. Control may be exercised by something as simple as a resistor on a switch or something as sophisticated as a microprocessor-controlled circuit operating based on a sophisticated, programmed application. For example, the controller may include a processor programmatically controlling the value of resistance in the circuit. The fluid delivery system 10 may also include a sensor (not shown) operably connected to provide inputs to the processor to control the value of resistance in accordance with an algorithm therewith.

In one embodiment of the fluid delivery system 10 at least a portion of the controller is located separately from the galvanic cell and is in communication with the cell by at least one of mechanical hardware, electromagnetic, radio frequency, magnetic, or optical feedback or circuit. In other embodiments, the controller is located inside the reservoir 22.

In operation, the gas generator 20 acts to fill the reservoir 22 in a controlled manner. Accordingly, the reservoir 22 will expand with the volume and pressure of the gas generated by the gas generator 20. Accordingly, the reservoir 22, contained on one side by a shell 24 or half 24 of the housing 18, may expand to displace the fluid source 26. The fluid source 26 in contact with the reservoir 22 is thus compressed between the reservoir 22 and a wall of the housing 18, resulting in expression of the fluid. Accordingly, the housing 18, together with the reservoir 22 and the fluid source 26 may be referred to throughout the specification as a pump 12.

The fluid source 26 within its shell 28 or half 28 of the housing 18 may actually contain any type of fluid. In one example, gas, liquid, or gel of suitable consistency and chemical composition may dispense from the fluid source 26.

In certain embodiments, a fluid may be loaded in the fluid source 26 at a manufacturing plant. The fluid source 26 may there be sealed to maintain a sterile condition until use. In an alternative embodiment, the fluid source 26 may be filled on site or at point of use by a doctor, pharmacist, or other medical professional responsible.

Either factory filling or onsite filling may use a fill port 30. Cost and security for a pre-filled fluid source 26 may militate against having a fill port 30. However, for a fluid source 26 designed to be filled or at point of use, a fill port 30 may be provided with an access 32 or inlet fixture 32. In one embodiment, the access 32 may be a septum 32 through which a syringe may penetrate to fill the fluid source 26. The fill port 30 may be made of a material of sufficient hardness and length to receive a needle without risk of puncture. The fill port or may alternatively be a luer lock type.

The fluid source 26 may be formed of any material that will contain the liquid but not actively affect the contained fluid, for example, polyethyleneteraphthalate (PET). In certain embodiments, various other polymers such a polyethylene, polypropylene, polyvinylchloride, or the like may be suitable. However, in general, the nature of the material of the fluid source 26 should not admit any harmful substances or reactions to the contained fluid.

This is particularly important for situations where the fluid source 26 may sit on a shelf, filled with a fluid, for a considerable period of time. For example, in a factor-sealed fluid source 26, the shelf life of the fluid must be configured along with the shelf life of the chemical constituents, plasticizers, and other chemicals that may be leached from the wall of the fluid source 26 into the fluid of the fluid.

In one embodiment of a method and apparatus in accordance with the invention, a medical professional may draw a fluid into a syringe. The syringe may be fitted to a needle or other injector to penetrate the septum 32 or access 32 to the fill port 30. A suitable amount and concentration of a prescribed fluid may fill the fluid source 26 to a suitable level required to service the dressing 16 for a predetermined time.

The volume added to the fluid source 26 may completely fill the fluid source 26. Alternatively, the amount of the fluid added to the fluid source 26 may exceed the capacity thereof. For example, the apparatus 10 may be "jump started" by adding a bolus of fluid to fill the fluid source 26, the feed conduit 14, and some portion or all of the dressing 16. Thus, the dressing 16 may be pre-loaded or even pre-saturated by a fluid when first loaded. Repeated boluses are possible.

Likewise, in certain embodiments, the apparatus 10 may be filled by an individual patient. For example, many superficial wounds such as scrapes and lacerations may benefit from an over-the-counter (OTC) solution, salve, oil, antiseptic, antibiotic or the like. Accordingly, an OTC version of the apparatus 10 may be either pre-filled or filled by a user with an OTC fluid.

In service, the apparatus 10 may feed a fluid from the fluid source 26 out through an exit port 34. The exit port 34 may be provided with a fitting 36 adapted to accomplish one or several functions. For example, the fitting 36 may include a check valve to prevent any back flow of the fluid from the feed conduit 14 into the fluid source 26. Likewise, the fitting 36 may include an orifice or other metering device to limit the flow of fluid to a particular rate.

A regulator, check valve, or pressure-relief valve may be part of the fitting 36 to maintain a certain pressure within the fluid source 26. The regulator may be outside of, partially within, or completely within the fluid source 26. Pressure in the fluid source 26 may be particularly important to precise control of delivery. It may need to increase when operating with particular fluids. Perhaps most frequently, regulation of pressure may resist wide fluctuations in the rate of delivery of the fluid.

For example, barometric pressure, ambient temperature, and the like may directly affect the pressure of gas in the reservoir 22. Wide fluctuations in either may be counterproductive to precise metering of a fluid through the fitting 36. If a pressure-regulation valve is located within the fitting 36, or otherwise associated therewith, comparatively higher pressure reduces sensitivity of the fluid source 26 or reservoir 22 to ambient pressure and temperature. For example, a bolus dose is not administered simply as a result of an increase in ambient temperature increasing the volume of the gas in the reservoir 22.

Thus, in one embodiment, the fluid source controls a fluid flow to dressing 16 or to a distribution member 40. The flow rate may be continuous or discontinuous. A discontinuous flow rate may be one that turns off and on over a period of time. A discontinuous flow rate may also be one provided under the variable force of a syringe. In one embodiment, flow rate may be programmatically controlled by a controller. The program may account for fluid flow patterns, either pre-selected or arbitrary, valve, conduit size, and other flow control parameters.

In general, an aperture 38 in either shell 24 of the housing 18 may provide access to a button to control operation of the gas generator 20. The aperture 38 may be closed with a cover, seal, diaphragm, or the like. For example, a rubber cover may fit within the aperture 38 resisting entry of dirt, dust, moisture, and the like into the housing 18. Nevertheless, a cover of thin, flexible, elastomeric material allows a user to apply pressure to a control button of the gas generator 20.

In certain embodiments of an apparatus and method in accordance with the invention, a cover member 39 or protective member 39 of a dressing 16 may provide one or more useful functions. For example, the protective member 39 may be opaque in order to prevent unsightly appearance of the dressing 16. By the same token, the protective member 39 may be transparent in order to provide easy monitoring. One may observe direction the distribution of the fluid throughout the dressing 16, as well as any seeping of blood or serum back into the dressing 16 from a skin defect being treated.

Likewise, a protective member 39 may typically resist abrasion, snagging, and other contact or contamination damage to itself and the underlying distribution member 40. Other members may exist within a dressing 16. Nevertheless, a protective member 39 may resist abrasion, transport of fluid, dirt, puncture, or the like. Likewise, the protective member 39 may be perforated or porous to permit access of air to a dressing 16.

The protective member 39 may be liquid proof to prevent escape or wicking of a fluid or other liquid in the dressing 16 into clothing, bedding, or the like. In certain embodiments, the protective member 39 may be microperforated or formed of some suitable material that permits passage of oxygen, water vapor or other gases while resisting passage of liquids.

Typically, a distribution member 40 holds a fluid delivered from the fluid source 26 through the feed conduit 14. The porosity of the distribution member 40 provides distribution of comparatively aqueous like fluids throughout. Meanwhile, the generation of gas from the gas generator 20 into the reservoir 22 applies both pressure and volume variation into the fluid source 26, driving a flow of fluid at some desired, engineered rate into the dressing 16. Thus, the fluid source may control the fluid flow to the distribution member 40. In one embodiment, the feed conduit 14 is connected to the fluid source 26 for replenishing the fluid in the distribution member 40, with or without additional human intervention.

The housing 18 may be relieved at selected locations to form, for example cradles 42, 44 capturing the fill port 30 and exit port 34, respectively. The cradles 42, 44 thus permit location of the access (inlet) fitting 32 and outlet fitting 36 outside the housing 18. The fitting 36 may be adapted to fit into or around the feed conduit 14.

The feed conduit 14 may feed into a feed line 48 passing into the dressing 16. An inlet port 50 the center of the area of the dressing 16 may distribute the fluid throughout by capillary action the distribution member 40 of the dressing 16. In certain embodiments, a manifold (not shown) may be used. Without a tailored capillary capability in the distribution member 40, distribution of a fluid throughout the dressing 16 may be enhanced by distributing throughout the distribution member 40 through a manifold. The manifold may be configured in any suitable manner. It will be appreciated by those of skill in the art that the feed conduit may be part of the dressing 16 itself.

For example, a large plenum having substantial area or a long linear path may present little resistance to flow of the fluid. A larger pressure drop would then occur as the fluid exits through perforations or other flow-limiting orifices. Alternatively, a manifold may have apertures sized to control or balance out pressure along several paths of distribution through tubes within the manifold. These apertures may provide the major, substantial, pressure drop between the pressure upstream of the manifold, and the ambient pressure in the dressing 16.

Figure 2:
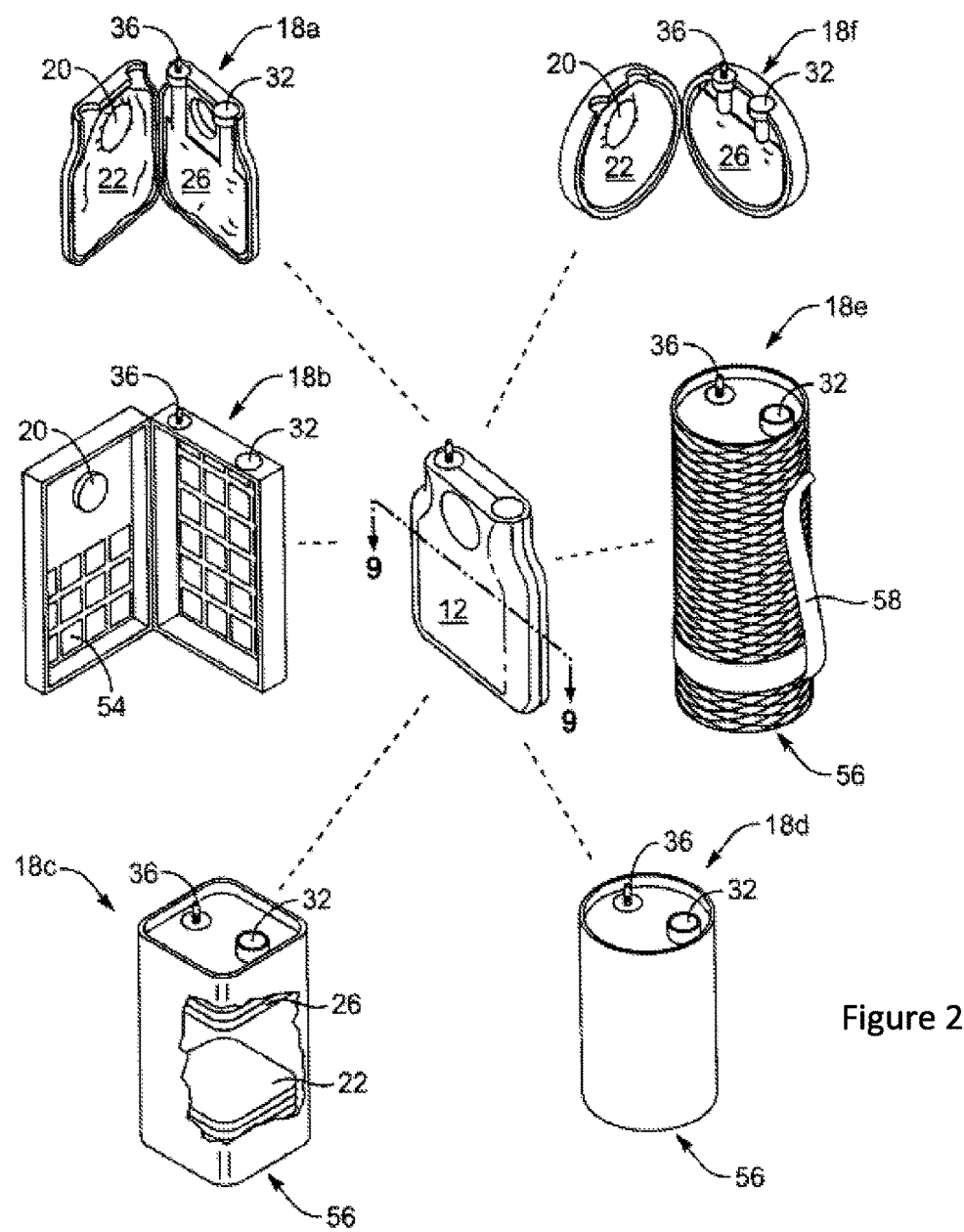
FIG. 2 is a perspective view of various alternative embodiments of a pump configured for use in a fluid delivery system and method in accordance with the invention.

Referring to FIG. 2, various embodiments of the housing 18 may capitalize on manufacturing methods, optimization of costs, ease of manufacturing, simplicity of operation, weight, shape, or the like. For example, the housing 18a provides an aspect ratio of thickness to width or thickness to height sufficiently small to fit readily into a pocket. Thus, an active outpatient, wearing of a dressing 16 may remain active. A comparatively thin, unobtrusive, housing 18*a* fits easily into a pocket of any article of clothing.

Likewise, the housing 18*b* may have a lightweight, clam shell configuration. A lattice 54 sufficient to contain the reservoir 22 and fluid source 26 may not provide puncture proofing for reservoir 22 and fluid source 26. However, if puncture is not a practical threat to the integrity of an apparatus 10, the lattice 54 may provide an appropriate wall. The housing 18*b* reservoir 22 and fluid source 26 are not shown, for clarity, but may fit the gas generator 20 and the inlet fitting 32 and outlet fitting as with the housing 18*a*.

Each of the housings 18 may be made of suitable size to match the administration of a fluid, ease of use, and carriage needs. For example, a comparatively thinner housing 18 may operate best when the reservoir 22 and fluid source 26 are placed side by side. If the reservoir 22 and fluid source 26 are placed end to end as in the housing 18*c*, then the aspect ratio of width to thickness at one end 56 of the housing 18*c* may be closer to one. The length of the housing 18*c* may be selected to promote complete expansion of the reservoir 22 and fluid source 26. The gas generator 20 filling the reservoir 22 may have a button on the outer wall of the housing 18*c*, or on one end 56. Alternatively, access to the gas generator button may be on the same end of the housing 18*c* as the inlet fitting 32 and outlet fitting 36.

In all the embodiments illustrated, the inlet fitting 32 is optional, depending upon whether a fluid is pre-loaded and sealed into a fluid source 26 by a manufacturer. If the fluid source 26 is filled or refilled at the point of use some access fitting 32 is required. However, the housing may be refillable with a pre-filled, sealed reservoir 22 and fluid source 26 in some embodiments.

The housing 18*d* may have a rounded, oblong cross section, an oval cross section, or a circular cross section. One benefit of a right circular cylinder shape is minimizing the overall dimensions of the housing 18*d*. Greater volume requires less surface area material if shaped like a sphere. Other shapes are improved as all the aspect ratios of thickness, to width, to length approach unity. Thus, a sphere is capable of holding the maximum volume with the minimum area of wall. Likewise, a right circular cylinder provides a better or greater volume per unit of area of wall then does a rectangular container. Nevertheless, various considerations, including convenience, mobility, and the like may be used to determine what shape, aspect ratios, and materials may be used in each of the housings 18.

In certain embodiments, the housing 18*e* may be formed of one or more lightweight materials and may even be flexible. For example, the housing 18*e* may actually be formed of a sparse lattice work of a polymer or fiber-reinforced polymer to sustain only internal pressure, not external pressure. Alternatively, the housing 18*e* may be formed as a filament-wound composite material of resin and reinforcing fibers having comparatively (compared to volume changes of liquid with ambient temperature, for example) very rigid walls in tension and compression, even sustaining very high pressures of many atmospheres.

For example, in certain embodiments, the exit port 34 may include a fitting 36 containing a tiny orifice sized to meter flow of a fluid. The housing 18*e* may sustain pressures of several atmospheres. At higher operating pressures than atmospheric, the effects of barometric or other environmental pressures and temperatures are significantly reduced. The housing 18*e* may have aspect ratios of a pocket pen, or small pocket accessory. A retainer 58 or clip 58 may secure the housing 18*e* to a pocket, clothing, bedding, or other suitable location. Engineered selection of aspect ratios of diameter to length for any housing 18 may promote unobtrusive location in clothing, bedding, or the like. Reliability of sealing and operation of the reservoir 22 and fluid source 26 has advantages with circular seals.

The housing 18*f* has an advantage of providing no substantial corners and a comparatively small aspect ratio of thickness to diameter, suitable for carrying in a purse, pocket, or the like. Meanwhile, manufacturing of the reservoir 22 and fluid source 26 may be simplified, and sealing thereof readily adaptable to various manufacturing processes.

Figure 3:
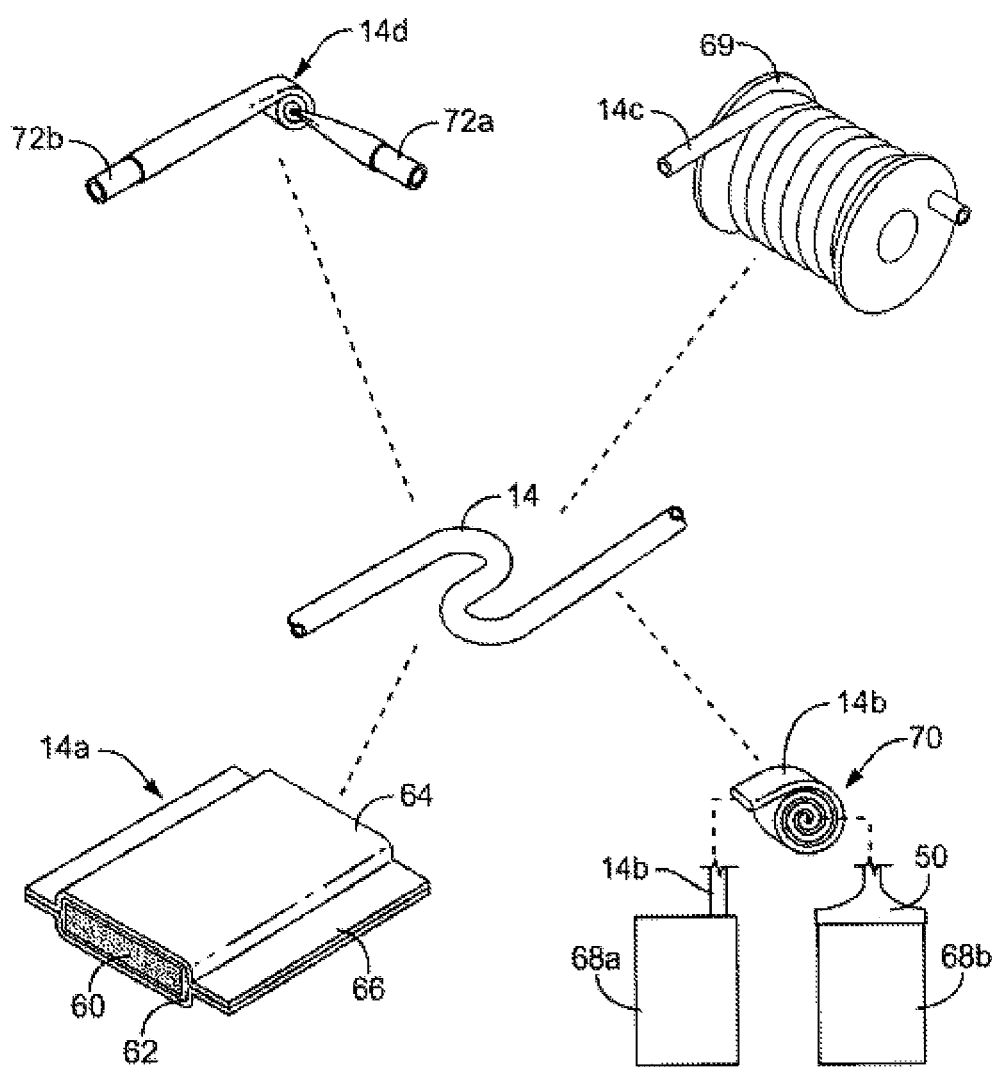
FIG. 3 is a perspective view of various alternative embodiments of feed conduits for conducting a fluid from a pump in accordance with the invention.

Referring to FIG. 3, a feed conduit 14 may optimize any parameter affecting cost, deployment, operation, durability, reliability, or the like. In the illustrated embodiments of FIG. 3, feed conduits 14 may have a round, or comparatively flat aspect. For example, the feed conduit 14*a* may include a very inexpensive bottom layer 62 and top layer 64 sealed together along a flange portion 66. The interior 60 of the feed conduit a may be completely empty, forming a tube. The feed conduit 14*a* may be formed of plastic film, plastic-coated paper, foil-coated plastic, or the like. Accordingly, the feed conduit 14*a* may be provided in a roll.

Alternatively, the feed conduit 14*a* may be cut to length or have fittings on either end preformed to interface with the outlet fitting 36 and the feed line 48 of a dressing 16. A fixture adapted to the outlet fitting 36 or feed line 48 may speed handling, connection, and sealing. In yet another alternative, the fluid source 26, feed conduit 14, and dressing 16 may be formed as an integrated, connected unit for disposable use. For example, polymer-coated paper may serve the structural and protective functions of all three components.

In one embodiment the feed conduit 14 may be filled with a core 60 or the like. For example, the cross-sectional area compared to the length of the feed conduit 14*a* may be extremely small. The flanges 66 may more easily sustain internal pressure, if enclosed volume is minimized within the feed conduit 14*a*. This corresponds to a filled cross section that is round or square and relatively small.

A core 60 may provide wicking from the outlet fitting 36 to the dressing 16 for several reasons. For example, in certain embodiments, pressure drop through the length of a feed conduit 14 may be desirable. By providing a rather tortuous path in a core 60, pressure in the fluid source 26 is not the direct driving force for transport. Rather, evaporation in the dressing 16 may draw the fluid by capillary action, replenishing liquids. Thus, the core 60 may provide regulation and replenishment automatically as needed.

Evaporation of liquid from a dressing 16 may provide a means of replenishment of the active suspended or dissolved therein. Thus, one way to assure an adequate concentration of an active ingredient in the fluid in the dressing 16 is to provide a comparatively volatile liquid that will evaporate from a dressing 16. Accordingly, as the carrier liquid evaporates, the fresh fluid is drawn in, having the concentration available from the fluid source 26.

In certain embodiments, the entire dressing 16, feed conduit 14, and fluid source 26 may be embodied in a single integrated system 70. For example, the volume 68*a* may be directly formed or sealed at a factory as a fluid source 26 to be placed in the housing 18 with the feed conduit 14*b* protruding there from. The feed conduit 14*b* may then conduct the fluid toward a header 50 or manifold 50 servicing a dressing 16 embodied as the distribution member 68*b*. It will be appreciated by those of skill in the art that the distribution member 68*b* may be designed or have the same characteristics as the distribution member 40 discussed above. The entire system can be sealed at a factory, and filled at point of use, or filled at the factory.

If filled at the factory, a seal may be required to close the reservoir 68a against leakage into the feed conduit 14b. If filled at point of use, the entire assembly may be shipped dry. The disposable fluid source 26, 68a may be filled at point of use including optionally priming both the feed conduit 14b and the distribution member 68b of the dressing 16, as desired. The end 68b may be an entire dressing assembly 16, including a distribution member 40.

The feed conduit 14b illustrates one embodiment in which the feed conduit 14 may be rolled flat. The entire assembly 70 may be rolled flat together or rolled together about the distribution member 40, 68b or dressing 16, 68b. The feed conduit 14b may be formed of any suitable material, whether paper, film, foil, other laminates, or the like. Meanwhile, in the illustrated embodiments, the feed conduit 14b may be have an integrated distribution member 68b or dressing 68b. The distribution member 68b may be fed directly by the feed conduit 14b, or by the feed conduit 14b through a manifold 50. Likewise, the distribution member 68b may be the same as a wicking layer 14 of a dressing.

For example, in certain embodiments, the dressing 16 may be formed flat of plastic film, plastic-backed paper, foil-lined paper, or foiled plastic. The distribution member 40, 68b or perhaps the entire dressing 16, 68b, may be formed integrally at manufacture with the feed conduit 14b. When the dressing 16, 68b is packaged, it may be sealed up and maintained sterile along with its entire feed conduit 14b.

If an integrated dressing 70 is formed to include the fluid source 26, 68a, distribution member 40, 68b and intervening feed conduit 14b, deployment may be simplified. Upon deployment, no sealing or connection is needed between the fluid source 26, 68a, feed conduit 14b, and the distribution member 40, 68b or dressing 16, 68b.

Fittings may be adapted to the feed conduit 14b to readily connect or may be unnecessary by forming all as a single containment. Upon opening, the integrated system 70 provides a fluid source 26, 68a fitting within the housing 18, a feed conduit 14b exiting through an appropriate cradle 44, and a distribution member 40, 68b or dressing 16, 68b at the opposite end.

A simply activated or rupturable seal may secure the fluid source 26 against any transfer of fluid to the feed conduit 14b prior to application. In one embodiment, the outlet fitting 36 may be combined with the access fitting 32. For example, injection through a septum 32 may provide piercing of a plastic seal to the fluid source 26 in order to permit filling, or simply to permit emptying. Thus, whether prefilled or filled at point of use, the fluid source 26 may be connected to the feed conduit 14b as an integrated assembly relying only on the housing 18 and gas fluid source 22 supplied also at point of use.

In certain embodiments, tubing 14c may provide a feed conduit. Such tubing may be provided on a reel 69 in bulk, or in a coil suitable for implementation as a plumbing project at point of use. In certain embodiments, the fitting 36 may easily be connected to a feed conduit 14c formed of a polymer or elastomer suitable to form a sealed, snug fit with the fitting 36. Likewise, the feed line 48 may provide sufficient structural stiffness, elasticity, or both to receive a feed conduit 14c snugly fitted there around.

The feed conduit 14d may be formed as flat tubing formed of a plastic film, elastomeric material, treated paper, plastic film reinforced by paper, or the like. In the illustrated embodiment, the feed conduit 14d may be provided with tips 72 or fittings 72 to act as seals, and as spreaders to open the feed conduit 14d. The fittings 72 support connection of the feed conduit 14d to the fitting 36 of the pump 12, as well as to the feed line 48 of the dressing 16. A predetermined length of feed conduit 14d may minimize cost and still maintain reliable sealing between the feed conduit 14d and its associated fitting 72a, 72b. The fittings 72 may provide a very low cost solution to delivery of fluid from the fitting 36 to the dressing 16.

Figure 4:
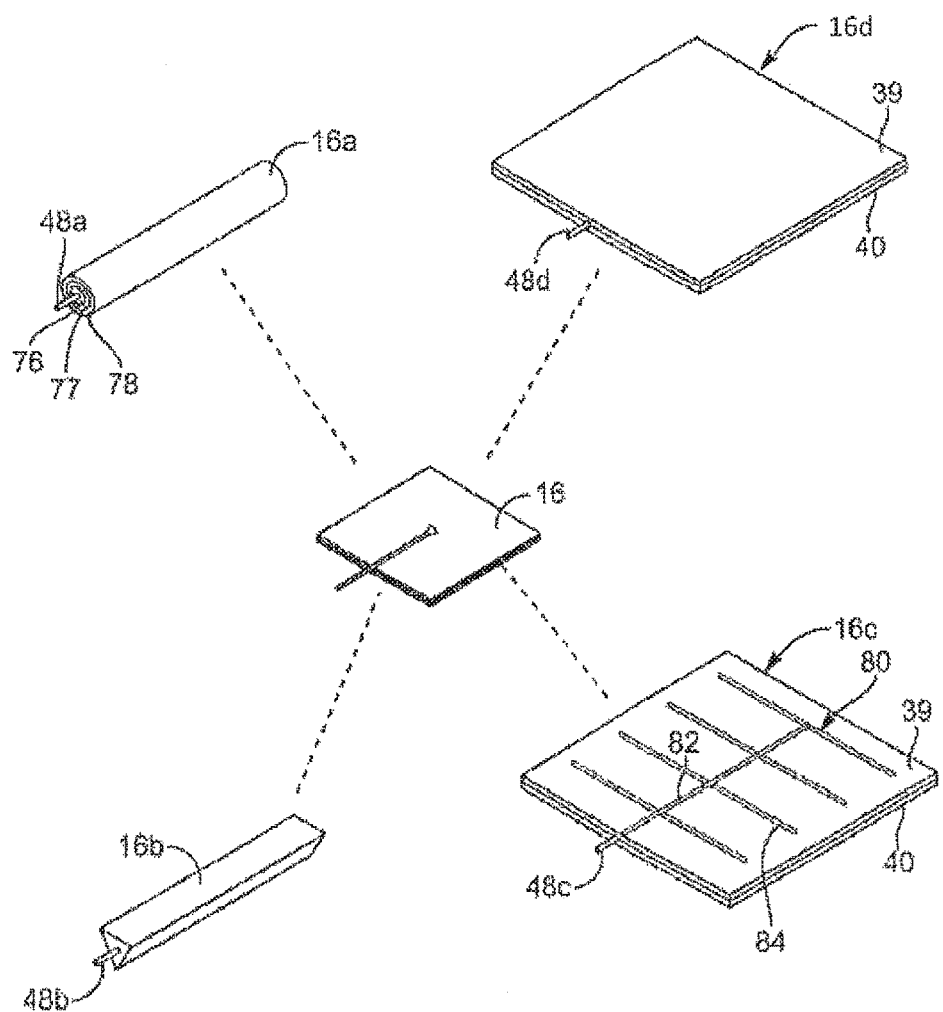
FIG. 4 is a perspective view of various configurations of a dressing for use in a fluid delivery system and method in accordance with the invention.

Referring to FIG. 4, the geometry of a dressing 16 may be configured for generic or specialty purposes. For example, in certain embodiments, a dressing 16a may be formed in a cylindrical configuration. A bulky shape may be required to fit within a wound that must heal itself closed, rather than be sutured closed.

In accordance with certain aspects of the invention, various layers 76, 77, 78 may provide differing benefits. For example, an interface member 78 may be provided as a non-adhering layer. For example, under the brand name TELFA™ a micro-perforated non-adhering polymer film is used in bandages. A TELFA™ layer may be appropriate for the interface member 78. In one embodiment, the interface member 78 is or contains a non-adhering polymer. In another embodiment, the interface member 78 may be or contain a bioabsorbable polymer. In one embodiment, the interface member 78 includes one or more of the following structures, either alone or in combination: a sheet, foam, a gel, gauze, a porous matrix, a honeycomb, a mop of fibrous material, a comminuted fibrous material, and a tubular structure. It will be appreciated by those of skill in the art that the interface member 78 may be made of other materials known not to adhere to a skin defect.

In one embodiment, the interface member 78 is a self-destructive material that can peel away from an adjacent layer or member, such as the distribution member, when the dressing 16 is removed from the skin defect and be left behind on the skin defect. For example, in one embodiment, a gel may control adhesion and self-destruct to prevent adhesion, so long as properly hydrated by the fluid. In other embodiments, the interface may be dissolvable or absorbable over time. The interface member 78 may also be configured to separate from the skin defect when the dressing is removed.

Meanwhile, the distribution member may comprise a "smaller pore size" wicking layer 77 that may distribute a fluid to skin defect through or without an interface member 78 and a "larger pore size" an inner layer 76 that may transport fluid by capillary action also, but with less resistance to flow. Nevertheless, the higher effective distance (larger pore size) across porosity in an inner layer 76 may provide less orientation-independence.

Likewise, a difference in pore size provides a net draw of liquids from areas of larger pore size to areas of smaller pore size. Thus, an inner layer 76 may receive a fluid from the feed line 48a. Accordingly, the inner layer 76 may distribute readily the fluid to the principal wicking layer 77. The principal wicking layer 77 may assure even distribution thereof.

Likewise, the dressing 16b may be configured geometrically to fit any particular application. Typically, wounds that are not of a serious or persistent nature may be closed by suturing. By contrast, chronic wounds, and wounds that may be subject to infection may be allowed or required to heal themselves closed, or may be closed only after infection has been eliminated or sufficiently reduced. Accordingly, a dressing 16b may be formed to fit within an open wound, thus delivering fluid by contact against the deep, affected, open surfaces of the wound.

The manufacture of the dressing 16b may begin with a cylinder, such as the layered cylinder of the dressing 16a. The cylinder 16a may then be molded, embedded with holding agents, stitched, heat set, or otherwise shaped as desired. Accordingly, the features of the dressing 16a may be implemented in a dressing of the configuration of the dressing 16b illustrated. Many specialty shapes may be made in this way to fit specific needs.

Many dressings are applied to surfaces covering and surrounding skin defects or wounds. For example, an injury may cause an open cut, laceration, scrape, burn, or the like. Likewise, an incision may leave a wound to be healed. In other circumstances, sores, boils, or the like may result in an open wound. The wound itself may need access to a fluid, but the surrounding area may also need a different treatment.

The area of a dressing 16c may be subdivided into regions. For example, a central region may contain the wound, and a surrounding area may be clear. In certain embodiments, two separate feed lines 48c may be provided to address two separate areas of a dressing. For example, if a wound itself needs an antibiotic, but a surrounding area needs an antiseptic, both may be delivered to different portions of a dressing 16c or two different dressings 16c.

In certain embodiments, a dressing 16c may receive a fluid through a feed line 48c into a plenum 82. The plenum 82 may act as a manifold 50 feeding various runs 84 or arms 84 distributing a fluid to the farther reaches of the dressing 16c. In the illustrated embodiment, the protective member 39 is shown as transparent in order to view the plenum 82 and runs 84.

As discussed hereinabove, the protective member 39 may be opaque, transparent, thin, thick, or otherwise configured to accomplish its function. Functions may typically be selected from preventing evaporation, promoting evaporation, providing resistance to abrasion, puncture, or other damage, providing access to air, providing protection from air, and so forth.

In the arms 84 or runs 84 off the plenum 82, perforations or other apertures may be selectively distributed. In certain embodiments, the entire network 80 may be porous yet resistant to leakage. For example, each of the plenum 82 and the runs 84 may be full of liquid dispensed only slowly and evenly throughout the dressing 16c via micropores driven only by pressure from the fluid source 26.

In other embodiments, the plenum 82 and arms 84 may actually be distribution tubes sized to receive and pass a liquid or other fluid readily, yet be sealed along their entire lengths except for an aperture at the end thereof. In certain embodiments, a dendritic or branching structure of the arms 84 may take on any suitable shape, whether rectangular, triangular, circular, polygonal, repeated bifurcating, or the like, and may branch sequentially any number of times.

For example, in certain embodiments, a tree structure may have a trunk or plenum 82, in which the branches 84 or arms 84 branch from one another, thus providing a network of distribution tubes. In certain embodiments, ends of the arms 84 may be drawn down or restricted in some other way in order to equalize pressure throughout, and provide control and distribution at an even rate throughout all of the end points or tips of the arms 84 throughout the dressing 16c. The distribution member 40 is then responsible to distribute from the arms 84 throughout itself in order to maintain a distribution of the fluid.

In general, the dressing 16d may include a protective member 39, a distribution member 40, and any other members need for distribution, promotion of flow, protection from outside environmental influences, protection against adhesion with the skin defect, or the like. Meanwhile, after penetration by the feed line 48d, the distribution system within the dressing 16d may take on any suitable form, such as those illustrated in FIG. 5.

Figure 5:
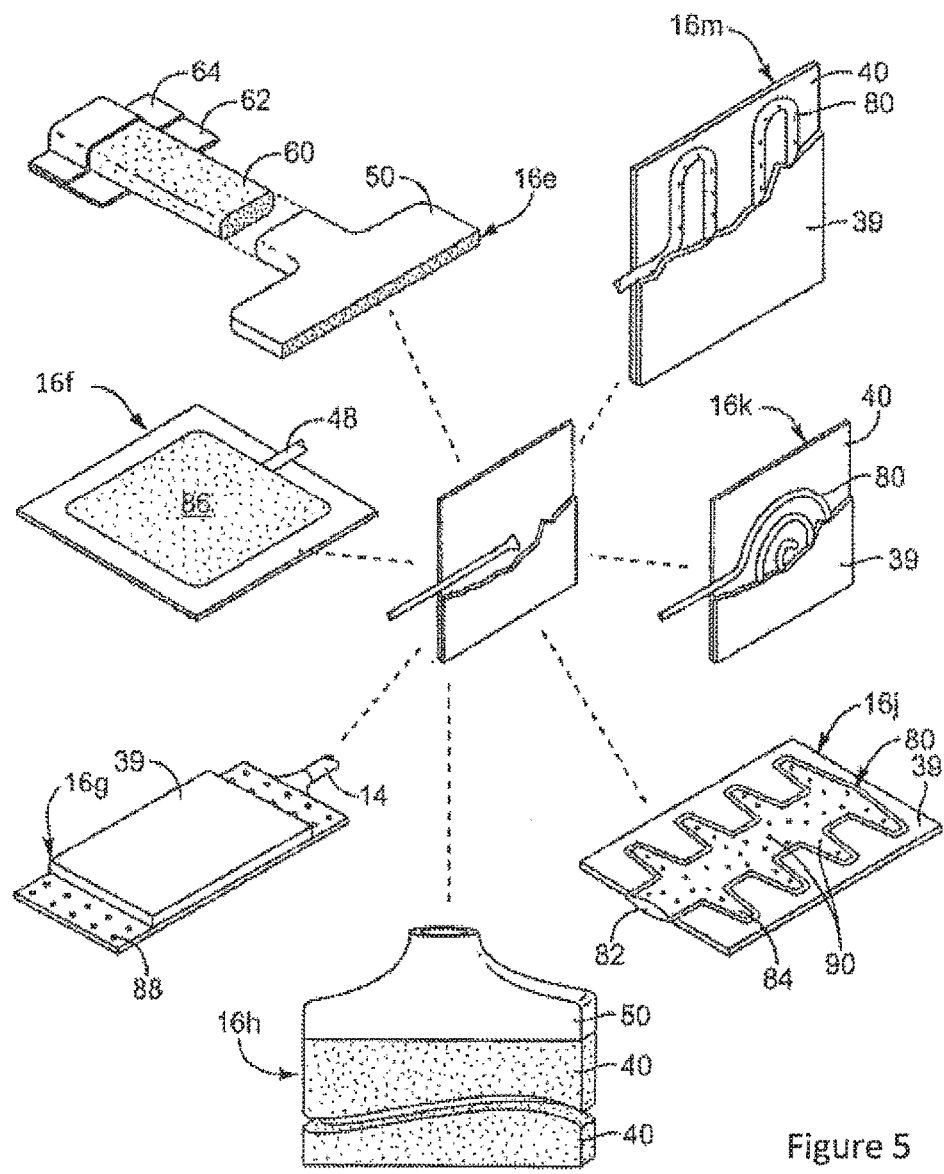
FIG. 5 is a perspective view of various embodiments of distribution systems within a dressing in accordance with the invention.

Referring to FIG. 5, various embodiments of a dressing are illustrated. For example, the dressing 16e may actually contain a distribution member with a layer fed by a manifold 50 contiguous and continuous with a core 60 of a feed conduit 14. For example, the feed conduit 14a of FIG. 3 provided an upper layer 64 and base layer 62 sealed to form a feed conduit there between. Either a cavity or passage may be provided or a wicking core 60.

In certain embodiments, a dressing 16f may be formed with a membrane 86 forming either a protective member, or a pocket. In certain embodiments, the membrane 86 may be formed as an envelope having distribution openings on the underside thereof against the distribution member 40 of a dressing 16f. For example, the feed line 48 may feed into a pocket-like membrane 86 having porosity only around the underside edges thereof. Likewise, the edges themselves may simply be perforated with small perforations tending to render the membrane 86 a large plenum.

The membrane 86 or membrane pocket 86 may be tacked through at certain location across its area, in order to prevent it from inflating in response to the pressure and presence of a fluid therein. Likewise, suitable perforations or other porosity may be sized and distributed across its underside, around its periphery, or along the perimeter of its underside in order to deliver a fluid into the underlying dressing 16f, or into the distribution member 40 of the dressing 16f.

The dressing 16g may include a protective member 39, and an underlying interface member 88. Between the protective member 39 and the interface member 88 may be a wicking material suitable for the function. Meanwhile, the feed conduit 14 may feed into the dressing 16g while the dressing itself passes fluid through the microporosity of the interface member 88.

In an alternative embodiment, for which the dressing 16g may also serve as an illustration, the protective member 39 of the dressing 16g may be the wick portion, while the interface member 88 serves as a plenum having a distribution of perforations to feed the fluid into the protective member 39. In accordance with the invention, a feed conduit 14 may feed into the interface member 88 formed as a hollow, flat, tube perforated to feed a protective member 39 which may be the wicking layer in this embodiment associated with the dressing 16g. In such an embodiment, a closed, flat, tubular membrane 88 may be perforated on one or both sides to feed into a distribution member 40. Thus, rapid distribution occurs along the comparatively larger volume available in flat tube 88. The tube 88 acts as a plenum 88, providing the fluid to the perforations crossing into the wicking layer, here represented by a protective member 39. Other members may be present in addition for other functionality as discussed hereinabove.

The dressing 16h formed of a wicking material such as a fiber, fabric, gauze, foam, or other material may be used alone. Alternatively, it may be used to assemble a dressing. In yet another embodiment, it may be located inside other members, such as between a barrier member and a non-stick member shown in FIG. 7. Accordingly, a full-width manifold 50 may provide an even distribution from an edge of a distribution member 40. The distribution member 40 may be engineered to standard or custom shapes, areas, thicknesses, widths, and lengths to meet the flow demands of a fluid to a particular skin defect. Sizes and shapes may include circular, rectangular, or cut-to-order for particular injured areas. In one embodiment, the distribution member 40 is configured to be cut to a desired size and still maintain a substantially uniform volume of fluid across the distribution member 40. Accordingly, in one embodiment, a cross-section of the distribution member is substantially the same and any other cross-section of the distribution member. It will be appreciated by those of skill in the art that multiple layers or members of the dressing 16 may cut individually or collectively to customize the size of the dressing 16.

In one embodiment, a dressing 16*j* may feed a distribution member (not shown) opposite a protective member 39. For example, a distribution system 80 or distribution tubes 80 may include a plenum portion 82 as well as various arms 84. In the dressing 16*j*, the plenum 82 or even the entire distribution network 80 may be formed of two layers of film. The side of the film fitted against the distribution member may have microperforations 90 sized to provide an even distribution.

The placement, size, and number of the perforations 90 may control the pressure drop from within the plenum portion 82 into the distribution member 40. Typically, however, the pressure differentials between the plenum portion 82, and the inside of the arms 84 may be comparatively quite small compared to the pressure difference between a fluid source 26 and a plenum 82. Accordingly, the distribution pattern of the perforations 90 may provide a limited number of outlets to control distribution into a distribution member 40.

In certain embodiments, a dressing 16*k* may have spiraling distribution tubes 80. For example, the distribution tubes 80 may be perforated along its entire path. The distribution tubes 80 may be configured as a spiral having a continuously decreasing cross-sectional area. Alternatively, the size of the internal diameter of the distribution tubes 80 may be constant, but the perforations may be comparatively smaller. Thus, the distribution tubes 80 become a plenum feeding out the fluid into the distribution member 40.

The distribution tubes 80 may have branches extending from the spiral. On the other hand, manufacturing may dictate a very simple configuration. Accordingly, a constant diameter and regular perforations of suitable size and distributed along its continuous length may operate adequately. Sealing one end of a perforated tubing, with the opposite end serving as a feed line 48 may provide a completely serviceable distribution tubes 80.

In certain embodiments, a dressing 16*m* may have a serpentine distribution tubes 80. Again, the serpentine shape may be formed of commercially available tubing, flat tubing, a pocket between layers of film or other material, or the like. Pressure drops may be engineered from the pressure of the gas in the reservoir 22 through to the pressure in the fluid source 26 holding the fluid, on to pressure drops through the exit port 34 and fitting 36 as well as the feed conduit 14. Meanwhile, the pressure dropped from the feed conduit 14 into any manifold 50 or distribution tubes 80 and on to the ambient environment of a dressing 16 may be engineered to make uniform the distribution in the illustrated embodiments.

One benefit of an engineered distribution member 40 of suitably small pore size is an independence from the effects of orientation. For example, in many circumstances, a dressing is assumed to lie horizontally. Accordingly, in theory, the entire dressing is at an even height. Thus, gravity effects do not alter dramatically the distribution of a fluid there throughout. Accordingly, the force exerted on the fluid by wicking action would be greater than or equal to the force exerted on the fluid by gravity.

However, in reality, many patients have skin defects located on vertical surfaces. For example, an outpatient may actually be active, walking about, engaging in athletic activities, while having a dressing 16 in place on an arm, leg, foot, torso, or the like. The effect of gravity is to bring a liquid down to the lowest contained altitude possible. However, by selecting the pore size, composition, construction, thereby creating specific hydrophobic/hydrophilic interactions, surface tension affect, or capillary force affect of the distribution member 40 an apparatus and method in accordance with the invention may provide independence of orientation.

Figure 6:
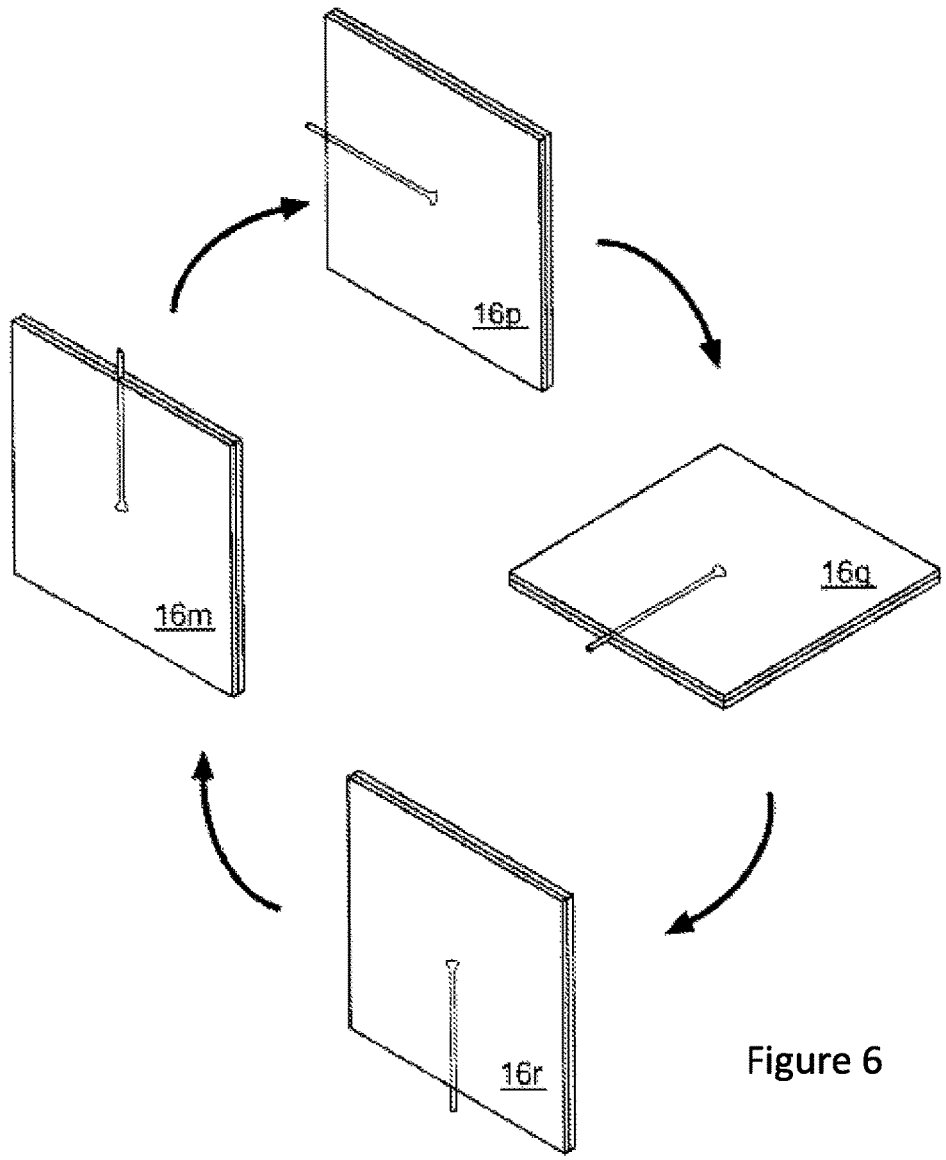
FIG. 6 is a perspective view of one embodiment of a dressing in various orientations that may be occupied during service in accordance with the invention.

Referring to FIG. 6, a dressing 16 may comprise a feed conduit (as shown and described in connection with FIGS. 1, 3, and 5 above) for delivering a fluid to a distribution member. The dressing 16*m* 16*p*, 16*q*, and 16*r* and distribution member receive and distribute the fluid substantially uniformly across the distribution member, irrespective of the orientation of the distribution member. The term "substantially uniformly" in relation to fluid distributed across the distribution member may mean that fluid is distributed to all parts of the distribution member 16. This may occur across a particular layer of the distribution member 16 or across all layers of the distribution member 16. "Substantially uniformly" may also mean that there is not significant pooling of fluid in one area of the distribution member while other areas of the distribution member have less fluid. "Substantially uniformly" may also mean the volume of fluid in one cross section of the distribution member is similar to the volume of fluid in other similarly sized cross sections of the distribution member. "Substantially uniformly" may also mean that the difference in fluid from section to section across the distribution member is small enough such that the application of the dressing 16 to the skin defect will result in consistent delivery to various areas of the skin defect.

The material of the distribution member 16 may allow for movement or the spread of fluid substantially uniformly across the distribution member by wicking action. The term "wicking action," "wicking," or "wick" as used herein throughout may include or may be used interchangeably with movement of fluid by capillary action, surface tension, hydrophobic action, hydrophilic action, or similar types of forces that can move a fluid. Orientation independence for example, may mean that the dressing 16*m* may be fed from the top and oriented vertically. The dressing 16*b* is oriented vertically, but fed horizontally, while the dressing 16*q* is oriented horizontally and fed horizontally. The dressing 16*r* is oriented vertically, and fed from below. In all of illustrated embodiments in FIG. 6, the orientation of the dressing 16 may be ineffectual to inhibit distribution.

In embodiment, the distribution member comprises at least one material chosen from a polymer, a woven fabric, a non-woven fabric, a naturally occurring fiber, a sponge, a fiber matrix, a gauze, absorbent material, adsorbent material, a gel, and a foam. In one embodiment, the distribution member 16 is a porous pouch.

Within the bounds dictated by physics and engineering, the capillary action of the distribution member 40 will draw a liquid upward. Also, "kiss-through" tacking of the outermost members of the dressing together will resist accumulation within the dressing. For example, a distribution member 40 may be bonded to a protective member 39 at regular intervals along a line, across a grid, or the like. Accordingly, two members not allowed to separate more than a nominal distance resist fluid accumulation.

However, by properly sizing the pore size composition, construction, thereby creating specific hydrophobic/hydrophilic interactions, surface tension affect, or capillary force affect of the distribution member 40, a dressing 16 may constructed of the distribution member 40 to effectively defy gravity and distribute the medicament, even upward from a location where introduced. Accordingly, the distribution member 40 may receive and distribute the fluid substantially uniformly across the distribution member, irrespective of the orientation of the distribution member.

In this embodiment, the distribution member 40 maintains a predetermined amount of fluid substantially uniformly across the distribution member. The distribution member 40 may in some configurations release fluid at a saturation point of level of the distribution member 40. In other embodiments, the release of fluid by the distribution member 40 may occur before or after that time. It will be appreciated by those of skill in the art that the rate and amount of fluid into the distribution member 40, coupled with the pore size of the distribution member 40 and the structure of adjacent members may be used to determine at what point the distribution member 40 may release fluid and also to what extent the fluid is distributed throughout the distribution member 40. It will further be appreciated by those of skill in the art that by having a distribution member configured to uniformly distribute fluid, or in other words, to have similar amounts of fluid occupy the different areas of the distribution member 40, that better application of the fluid to the skin defect can be obtained.

The distribution member 40 was tested in one test by applying the dressing vertically to a sheet of glass. An amount of colored fluid was applied to the center of the distribution member and the spread of fluid was recorded over time. Viewing the recording after various points in time revealed that fluid was radially distributed from the point of introduction uniformly in all section of the distribution member despite the down ward pull of gravity. Thus, at different points in time, the outer boundary of the spreading fluid created substantially concentric circles under the entire distribution member was filled with fluid. Dozens of tests were performed with substantially similar results.

The configuration of the distribution member 40 of the present embodiment may also allow the distribution member to maintain a concentration of active ingredient in the fluid substantially uniformly across the distribution member and allow said concentration of active ingredient in the fluid to communicate with the skin defect. The distribution member 40 may be engineered to allow the concentration of the fluid to be uniformly distributed across the distribution member. In other words, the distribution member 40 may allow fluid distribution such that a concentration of the fluid in one area of the distribution member is substantially similar to the concentration of the fluid in another area of the distribution member. By engineering the distribution member 40 and by choice of active ingredient carrier as discussed above, among other things, the distribution member may maintain a concentration of active ingredient in the fluid substantially uniformly within a predetermined range of concentration across the distribution member and may allow said concentration in said range to communicate with the skin defect. In one embodiment, the dressing 16 comprises a feed conduit for delivering a fluid to a distribution member 40. The distribution member 40 receives and distributes the fluid substantially uniformly across the distribution member 40, irrespective of the orientation of the distribution member 40. The distribution member 40 comprises material that allows the spread of fluid substantially uniformly across the distribution member 40 by wicking action and can be cut to a desired size and still maintain a substantially uniform volume of fluid across the distribution member 40.

Referring to FIG. 7, in certain embodiments, a dressing 16 may include one or many members to accomplish their respective functions. For example, in the illustrated embodiment, a member 92 may be a protective member 92. Protective members 92 are typically installed to prevent puncture, abrasion, snagging, evaporation, wetting, soiling, and the like. A protective member 92 may operate to provide multiple functions. It will be appreciated by those of skill in the art that the protective member 92 may be the protective member 39 discussed above.

For example, a durable fabric may be used as an protective member 92 to promote evaporation and aeration while still protecting against puncture, snagging, abrasion, wear, and the like. Meanwhile, other members such as polymeric materials may minimize access to air, optimize evaporation of fluids, or the like. Accordingly, the protective member 92 may be designed according to the functionality desired.

In certain embodiments, the member 93 may be a stay-dry (hydrophobic) lining. For example, because a wicking layer 95 will tend to draw a fluid from a transport wicking layer 94, the wicking layer 94 may need to be separated by a stay-dry liner 93. Accordingly, the lining member 93 rejects transport of liquids therethrough, therein, or both. Liquids preferentially stay in the wicking layer 94.

The functions of the members 92 and 93 may be reversed. For example, a stay-dry material may form the protective member 92. As a practical matter, the structurally protective member 92 typically serves best as the outermost member. Accordingly, the protective member 92, may itself need to be protected against wicking from liquids being transported in a wicking transport member 94. Thus, a stay-dry lining member 93 rejects the transport of liquid from the wicking layer 94 into either of the protective member 92 and the outside environment.

A stay-dry lining member 93 resists wicking into the protective member 92. For example, if a dressing 16 is laden with liquid fluid, typically saturated, then the fluid may be wicked out into such items as cotton bed clothes, bedding, and the like. Accordingly, a stay-dry lining 93 may resist the transport of liquid out of the transport wicking layer 94. If the protective member 92 is imperious to liquid, then a stay-dry linen member 93 may not be required.

On the other hand, where aeration or evaporation is desired, the protective member 92 may be primarily a mechanical protection, very porous and susceptible to absorbing liquid from an optional transport wicking layer 94. The wicking layer 95 is typically formed of a material having a smaller effective pore size than that of the protective member 92 or the transport wicking layer 94. Accordingly, the wicking material 95 preferentially attracts fluids from the transport wicking layer 94. Thus the wicking layer 95 may be the principle delivery member for the skin defect. The stay-dry member 93 may be integral with or one and the same as the protective member 92 and the protective member 92 may have all the characteristics and functionality of the stay-dry member 93.

Having two wicking layers 94, 95 is optional. Either may suffice. However a smaller pore size promotes delivery independent from orientation, while larger pore size promotes faster capillary transport. A member 94 may thus be thought of as a distribution member. The distribution member 94 may provide a pore size (e.g. interstitial gap, etc.) having less resistance to flow then the wicking layer 95. It will be appreciated by those of skill in the art that the distribution member 94 may also be the distribution member 40 and/or 68b described above.

Meanwhile, a non-adhering interface member 96 may cover the principal wicking layer 95 which may be part of the distribution member. The interface member 96 may be the same interface member 78 described above. Dimensions of the dressing 16 of FIG. 7 may be selected as appropriate. For example, the scales or sizes of the thickness of the non-adhering interface member 96 and the wicking distribution member 95 are effectively polar opposites. The non-adhering interface member 96 (if a solid polymer) is typically as thin as possible and perforated in order to promote transport of the fluid from the wicking layer 95. If the non-adhering interface member 96 is a gel, it may diffuse an active ingredient with or without the carrier to the treated skin defect. A gel may also largely liquefy or disintegrate (to a greater or lesser extent, depending on formulation) in the presence of liquids, promoting direct delivery of a liquid from a wicking layer 95 to skin defect.

In one embodiment, the interface member 96 is positioned between the distribution member 94 and a skin defect being treated by the dressing 16. The interface member 96 configured to transport the fluid into contact with the skin defect. The protective member 92 may be positioned adjacent to the distribution member 94. As discussed above, the protective member 92 may protect the distribution member 94 from loss of functionality. For example, if the distribution member 94 is damaged in some way or clogged or if the structure is altered, the distribution member 94 may not spread the fluid substantially uniformly. Furthermore, the protective member 92 may be semi-occlusive and may aid in directing fluid out of the distribution member 94 and onto the skin defect. Thus, the protective member 92 might ensure ability of moisture or vapors to leave the distribution member and to leave the dressing in order to balance the moisture content of the dressing and thus the fluid level balance in the skin defect.

Figure 7:
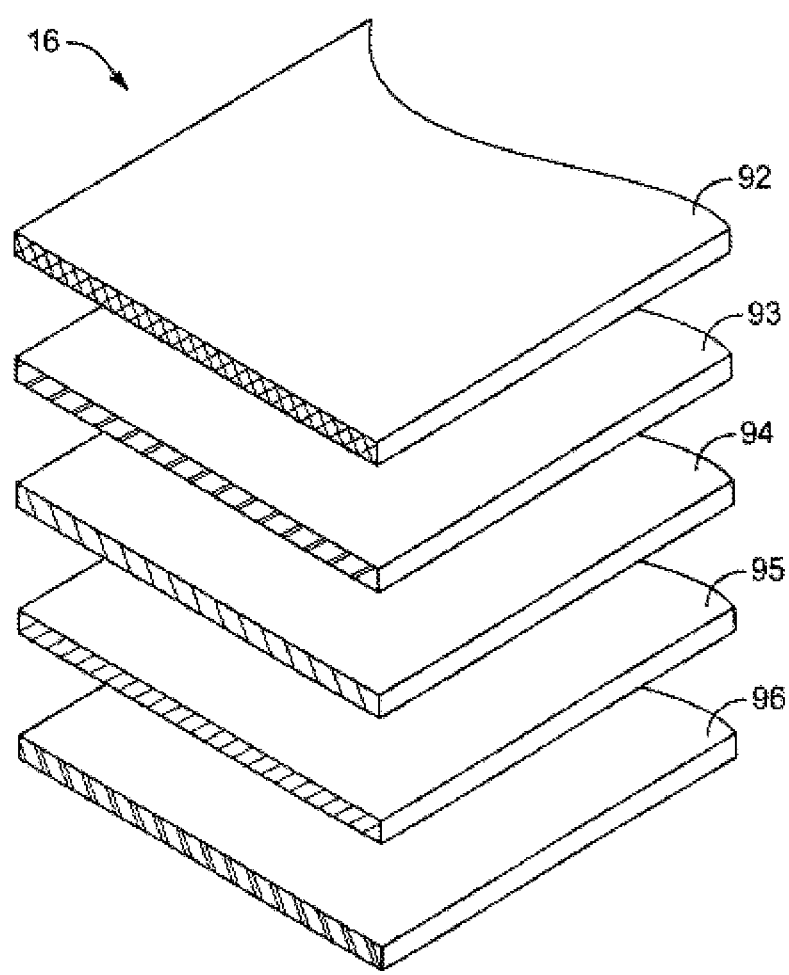
FIG. 7 is a perspective view of various members that may be consolidated to form a dressing in accordance with the invention.

The dressing 16 of FIG. 7 may be configured with any of the members 92-96 shown, some of them, or additional members, as desired. Typically, any of the dressings 16 discussed hereinabove may be made with one or more of the members 92-96 illustrated in the dressing 16. Accordingly, a multi member dressing 16 may be engineered to accomplish its functions in the most effective way by using the appropriate selection of members 92-96. The multi-member dressing may include a wicking layer receiving the fluid, a barrier member that may or may not be configured to protect the dressing from the environment and provide for vapor transmission, a transfer member to transfer the fluid to the distribution member, an fluid absorber member to absorb excessive fluid being delivered or for absorbing the wound exudate, a tenting member positioned at the rim of the dressing to provide for lateral evaporation, and an interface member between the wicking layer and the treated skin defect to transfer the fluid thereto from the wicking layer while performing any other function needed, such as sealing, anti-adhesion, or the like. Alternatively, the dressing may comprise at least one functional member consisting of a distribution member an interface member, a transport member, a protective member, and an absorption member. Any of said members could be integrated to achieve multiple functions in one or more members. Thus, one or more of the members 92-96 may be structured to operate as at least one of an interface member, a distribution member, a fluid transport member, a protective member, a tenting member, a fluid absorber, and a combination thereof.

Figure 8:
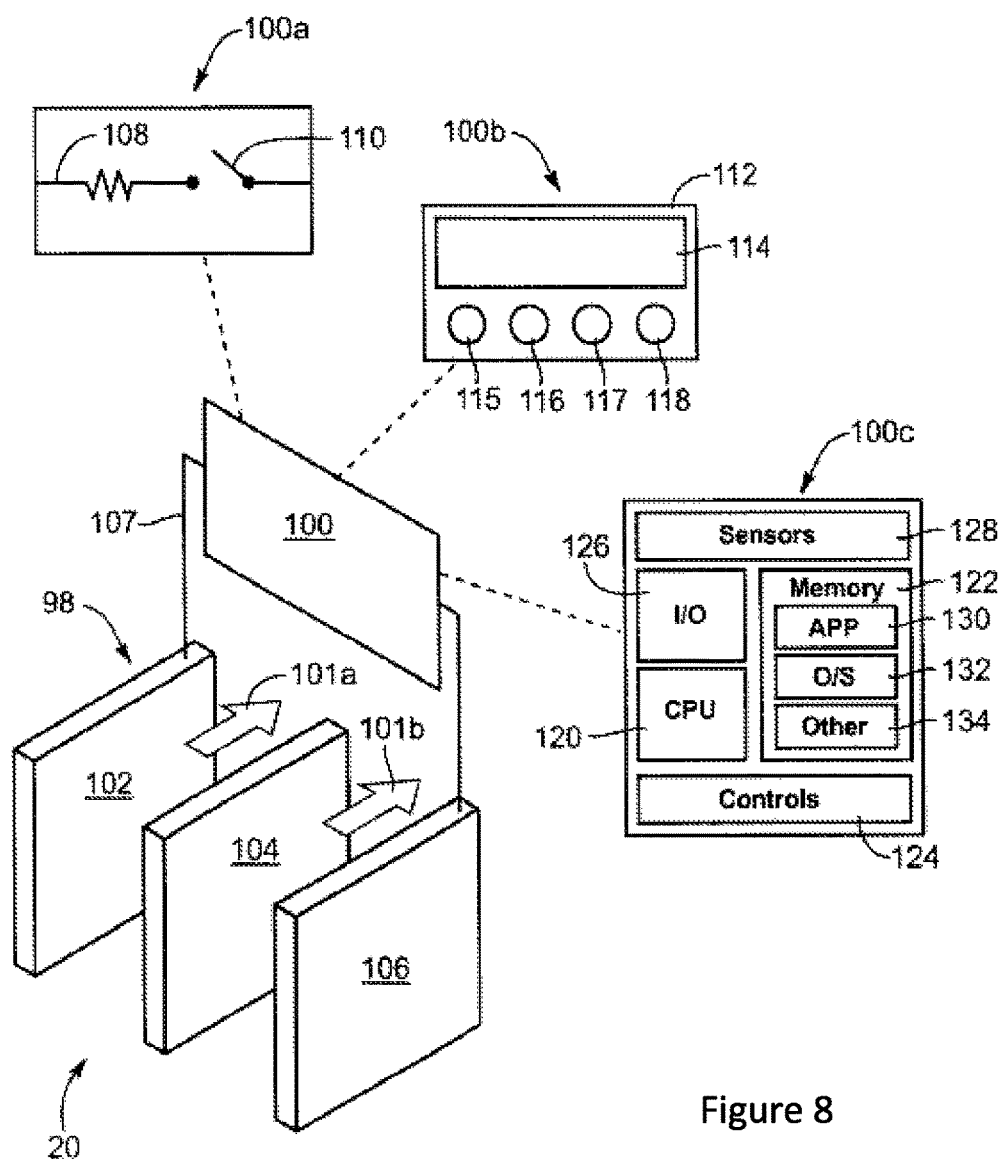
FIG. 8 is a schematic diagram of a gas generator with various alternative embodiments on the controller therefore in accordance with the invention.

Referring to FIG. 8, a controller 100 may control an electrochemical reactor 98 producing byproducts 101 or gasses 101. These byproducts 101a, 101b are generated in response to the spontaneous flow of electrons and ions in the electrochemical reactor 98 or galvanic cell 98. The active members 102, 106 may contribute or consume electrons. Either one may generate a byproduct 101 that becomes a gas for the reservoir 22 (FIGS. 1 and 2).

Often, one material 102, 106 may create a byproduct 101 as a gas, while the other material 106, 102 produces a byproduct that stays in solution or plates out at a surface of the other active material 106, 102. A separator 104 may or may not be used in-between the two active materials. Regardless of the chemistry, or the mechanism, the electrochemical reactor 98 may be made to generate a byproduct 101 in a gaseous state by choosing the chemistry of the electrodes 102, 106 and controlling the electrical current through a circuit 107.

In the illustrated embodiment, the electricity generated or the current generated through the circuit 107 is not the object, but rather the byproduct gasses that are discharged as a result of the flow of electrons. However, such a battery or galvanic cell 98 is designed to optimize the generation of the byproduct 101, rather than optimizing the output of electricity through the circuit 107.

The circuit 107 may control electron flow, and thus the generation of gas. In one basic embodiment, a controller 100a may include a switch 110 to close the circuit 107. To limit the rate of electrochemical reaction, and thus the generation of gas, some impedance 108, such as a resistor 108, may be in the circuit 107. Thus, a controller 100 in a simplest embodiment may simply be a module 100a or controller 100a providing a physical switch 110 and an impedance 108. In this embodiment, the switch 110 may selectively open and close.

In some embodiments, the switch may operate a single time to move from an open position to a closed position. In alternative embodiments, the switch 110 may selectively open again to stop generation of gas. In a more sophisticated embodiment, a controller 100b may include a control panel 112 having a display 114. A user may read instructions or bring up menus on the display 114. By various buttons 115-118 a user may select an "on" or "off" condition, provide a rate increase or decrease in the production of gas.

In general, a controller 100b may be a simple analog or digital circuit accomplishing certain limited functions. Likewise, the controller 110b may include additional sophistication.

For example, in one embodiment, a controller 100c may actually be a microprocessor-based controller 100c. For example, in the illustrated embodiment, a central processing unit 120 (CPU 120) may operably connect to a memory device 122. In a typical embodiment, the processor 120 may operate controls 124 such as relays, gates, and the like for increasing current flow from a very low rate through the circuit 107 to a very high rate.

In one contemplated embodiment, the processor 120 may receive instructions, data, or the like, through an input/output interface 126 (I/O interface). For example, sensors 128 may operably connect to provide inputs to the I/O interface 126. Sensors 128 may monitor pressures, humidity, chemical concentration, electrochemical properties, or the like from the dressing 16 or elsewhere in the system 10 and report through the I/O interface 126 to the processor 120 to control the device operation.

The processor 120 may be programmed with an application 130 stored in a memory device 122. Alternatively, the processor 120 may execute the application 130 to provide feedback control based on sensors 128 to control a value of a desired property, parameter, or condition associated with the dressing 16. For example the pump 12 may be controlled according to humidity sensed by a sensor 128 within the dressing 16. In such an embodiment, for example, a portion of the dressing 16 may be sensed to determine that the liquid of a fluid has evaporated or has a certain concentration of a chemical detected.

In general, the pump may be as simple or sophisticated as warranted by cost, medical constraints, or desired controls for applying a fluid to a dressing 16. In general, any physical parameter that may be sensed by a sensor 128 may be used to control the processor 120 through a suitable application 130 programmed to do so. Accordingly, more gas may be generated by the generator 20, prompting the flow of additional fluid from the fluid source 26 through the feed conduit 14 and into the dressing 16.

Typically, the application 130 will operate on top of an operating system 132 or O/S 132. Other functional features may be accomplished by other software 134 executed in the processor 120 based on data 134 in memory 122. For example, other data 134 may include a history of operation of the gas generator 20 by time, chemical, current, gas volume, or the like. So long as physical equations are known, they can be programmed into the application 130 to detect and store data 134. Data 134 may also include other applications such as supporting applications, control applications, data management applications, and the like.

Figure 9:
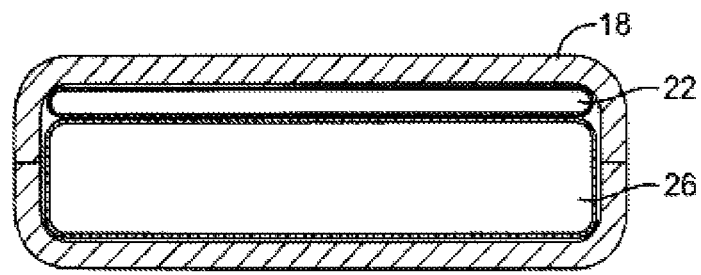
FIG. 9 is a side plan view of a cross-section of one embodiment of a housing and reservoir and fluid source system for a pump in accordance with the invention.

Referring to FIG. 9, a cross section of a housing 18 may include a reservoir 22 storing gas. Likewise, a fluid source 26 may contact a reservoir 22. Motion or pressure by the reservoir 22 will result in corresponding motion or pressure in the fluid source 26. Typically, the fluid source 26 may be pre-filled or filled at point of use. In the illustrated embodiment, the reservoir 22 and fluid source 26 may be installed such that initially the gas reservoir 22 occupies very little or comparatively little space. Meanwhile, upon filling, either at a factory or at point of use, the fluid source 26 typically occupies the majority of the space within the housing 18.

As gas is generated in the gas reservoir 22, it displaces space occupied by the fluid source 26, discharging the fluid through an outlet fitting 32 to a feed conduit 14 and on to a dressing 16. In the illustrated embodiment, the reservoir 22 and fluid source 26 may substantially occupy the available space within the housing 18. The reservoir 22 and fluid source 26 may have elastomeric properties. However, elastomeric materials may also react with certain fluids.

For example, many fluids involve extremely small amounts of an active ingredient in an overwhelming volume of a carrier. Meanwhile, an active ingredient may be very reactive. Thus, a trace amount of a metal or other contaminant may react with a large amount of an available active ingredient. Thus, the fluid source 26 is better served if made of less reactive materials.

The fluid source 26 should typically not have any deleterious effect on the fluid. Likewise, no constituent of the fluid's active ingredient, carrier, or other excipient should attack the integrity of the fluid source 26 during its operational lifetime. Accordingly, materials, sizes, and properties may be selected to provide an optimum chemical stability, mechanical integrity, pressure support, and so forth needed for the particular apparatus 10 and method contemplated.

In certain embodiments, the reservoir 22 and fluid source 26 may actually have elastic properties (e.g. elastic restrictions, spring pistons, etc.) and provide some resisting amount of pressure when inflated. Alternatively, the reservoir 22 and fluid source 26 may have a substantially fixed wall area, capable of enclosing a fixed maximum volume. Accordingly, as either the reservoir 22 or the fluid source 26 is filled, it may expand toward its maximum volume without substantial resistance until that point is reached.

Figure 10:
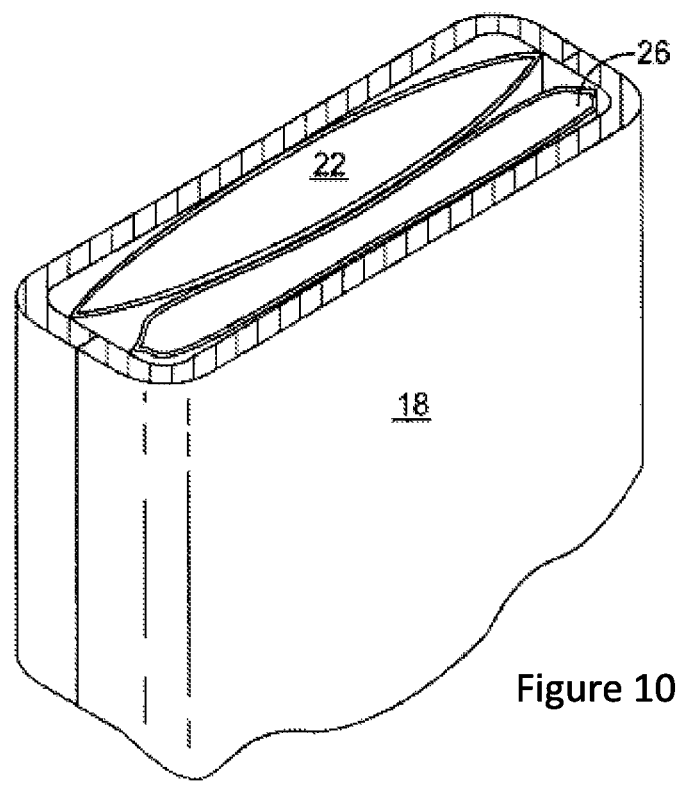
FIG. 10 is a perspective cutaway view of an alternative embodiment of a housing and enclosed reservoir and fluid source in accordance with the invention.

Referring to FIG. 10, a reservoir 22 and fluid source 26 may be formed of laminated or bonded layers of materials. The housing may be openable or sealed, disposable or re-usable. The reservoir 22 and fluid source 26 need not be limited to a single reservoir each within the housing 18. Multiple reservoirs 22 may be used or multiple fluid sources 26. Likewise, reservoir 22 and fluid source 26 may be replaceable, refillable, or both.

For example, in certain inexpensive embodiments, a very simple switch 100 may control a gas generator 20 filling a reservoir 22. The time may be fixed by the chemistry, size, and so forth of the principle elements 102, 104, 106 of the electrochemical reactor 98. A second reservoir 22, with a second gas generator 20 may be useful for operating the apparatus 10 a second time, after refilling of the fluid source 26. In such a way, a multi-use, disposable unit may still result with very primitive controls 100.

A method for treating a skin defect is also disclosed. The method includes providing a dressing or fluid delivery system comprising a feed conduit and a distribution member in fluid communication with the feed conduit. The distribution member is configured to receive a fluid and comprising a material to substantially uniformly distribute the fluid across the distribution member irrespective of the orientation of the distribution member. The dressings and delivery systems described in their various embodiments and combinations in this application may be used for the dressing or fluid delivery system used in the method treating a skin defect.

The method includes applying the dressing to a skin defect and supplying a fluid to the distribution member through the feed conduit. Supplying a fluid in one embodiment may include supplying a pre-determined quantity of fluid containing an active ingredient. Supplying a fluid may also include priming the dressing with a quantity of fluid. In another embodiment, priming the dressing with a quantity of fluid is a separate step. Supplying a fluid may also include providing a bolus of fluid to the dressing before or after an initial quantity of fluid is supplied. In one embodiment, supplying a quantity of fluid is provided manually from a fluid source to the dressing. In another embodiment, fluid is automatically provided from a fluid source to the dressing. In other embodiments, the dressing or system may include a controller of the type described herein which may be programmed to supply the fluid at a predetermined flow rate or time interval. The supply of fluid by any of these methods may be continuous or at intervals with varying flow rates.

The method includes the step of distributing the fluid substantially uniformly across the distribution member. The method also includes substantially uniformly distributing the fluid to the skin defect irrespective of the orientation the distribution member.

Supplying fluid to the distribution member comprises maintaining a fluid with a concentration of active ingredient greater than, equal to, or less than a predetermined threshold over a predetermined period of time. This may include maintaining the concentration of the fluid at a minimally therapeutically effective threshold throughout the distribution member. Supplying a quantity of fluid to the distribution member may be such that the skin defect receives a concentration of the active ingredient greater than a therapeutically effective threshold corresponding to a minimum inhibitory concentration.

It will be appreciated by those of skill in the art that it may be desirous to maintain the concentration of the active ingredient below a value corresponding to a maximum concentration above which the active ingredient causes side effects. Furthermore, a concentration of active ingredient may be selected to substantially minimize the development of resistance, by a target organism, to the active ingredient, throughout a pre-selected period of time. Maintaining a concentration of active ingredient in the distribution member above, at, or below a threshold, such that the desired concentration is applied to the skin defect may be beneficial to facilitate pain or inflammation reduction or to promote healing of the tissue.

The method may also include trimming or cutting the dressing or one or more layers or member that make up the dressing to a desired shape corresponding to a treatment area.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A fluid delivery system comprising:
   a pump comprising a housing having an interior volume, the interior volume being inextensible and vented to discharge gas therefrom, and containing a reservoir and a fluid source in contact with one another,
   the fluid source containing a fluid having a first wall flexible to move in response to substantially any pressure and substantially impervious to the fluid, and an outlet to dispense the fluid and
   the reservoir comprising a second wall, in contact with the first wall to move therewith, substantially impervious to gas; a galvanic cell in communication with the reservoir and comprising chemicals selected to produce a gas within the reservoir;
   a flexible wound dressing to expose the fluid to a skin defect of a subject, the dressing comprising a distribution member configured to receive the fluid and comprising a wicking layer to substantially uniformly distribute the fluid across the distribution member by wicking action irrespective of the orientation of the distribution member; and
   a feed conduit connectable to the outlet and in fluid communication with the distribution member to replenish the fluid in the distribution member.

2. The system of claim 1, wherein the wicking layer comprises a pore size selected to uniformly distribute the fluid across the distribution member.

3. The fluid delivery system of claim 1, wherein the fluid comprises an active ingredient.

4. The fluid delivery system of claim 1, wherein the dressing further comprises a protective member positioned adjacent the distribution member.

5. The fluid delivery system of claim 4, wherein the protective member is semi-occlusive.

6. The fluid delivery system of claim 1, wherein an interface member is positioned between the distribution member and the skin defect being treated by the dressing, the interface member transporting the fluid into contact with the skin defect.

7. The fluid delivery system of claim 1, wherein the distribution member comprises at least one material chosen from a polymer, a woven fabric, a non-woven fabric, a naturally occurring fiber, a sponge, a fiber matrix, a gauze, absorbent material, adsorbent material, a gel, and a foam.

8. The fluid delivery system of claim 1, wherein a force exerted on the fluid by the wicking action is greater than or equal to a force exerted on the fluid by gravity.

9. The fluid delivery system of claim 1, wherein the distribution member maintains a substantially uniform fluid volume across the distribution member and allows the fluid to communicate with the skin defect upon reaching or exceeding a predetermined saturation level.

10. The dressing of claim 1, wherein the distribution member maintains a concentration of active ingredient in the fluid substantially uniformly across the distribution member and allows said concentration of active ingredient in the fluid to communicate with the skin defect.

11. The dressing of claim 1, wherein the distribution member maintains a concentration of active ingredient in the fluid substantially uniformly within a predetermined range of concentration across the distribution member and allows said concentration in said range to communicate with the skin defect.

12. The fluid delivery system of claim 1, wherein the fluid source outlet comprises a regulator to maintain pressure in the fluid source greater than the ambient pressure to minimize operational variations due to variations in at least one of the ambient temperature, the barometric pressure, or the orientation of the device.

13. The fluid delivery system of claim 1, further comprising a controller connected to the galvanic cell in a circuit to control the generation of the gas in the reservoir, thereby controlling a delivery rate of the fluid from the fluid source.

14. The fluid delivery system of claim 13, wherein the controller comprises a fixed or variable resistor and a switch.

15. The fluid delivery system of claim 13, wherein at least a portion of the controller is located separately from the galvanic cell and is in communication with the cell by at least one of mechanical hardware, electromagnetic, radio frequency, magnetic, or optical feedback or circuit.

16. The fluid delivery system of claim 13, wherein the controller is located inside the reservoir.

17. The fluid delivery system of claim 13, wherein the controller further comprises a processor programmatically controlling the value of resistance in the circuit.

18. The fluid delivery system of claim 1, further comprising a fill port in fluid communication with the fluid source.

19. The fluid delivery system of claim 1, further comprising a sensor operably connected to provide inputs to the processor to control the value of resistance in accordance with an algorithm therewith.

20. The fluid delivery system of claim 1, wherein the wicking layer is adapted to distribute the fluid via evaporation.

* * * * *